US010195277B2

(12) United States Patent
Singh

(10) Patent No.: US 10,195,277 B2
(45) Date of Patent: Feb. 5, 2019

(54) SINGLE DOMAIN ANTIBODIES DIRECTED AGAINST HUMAN IMMUNODEFICIENCY VIRUS

(71) Applicant: SINGH BIOTECHNOLOGY, LLC, Tampa, FL (US)

(72) Inventor: Sunanda Singh, Lutz, FL (US)

(73) Assignee: Singh Biotechnology, LLC, Hudson, FL (US)

( * ) Notice: Subject to any disclaimer, the term of this patent is extended or adjusted under 35 U.S.C. 154(b) by 0 days.

(21) Appl. No.: 15/342,032

(22) Filed: Nov. 2, 2016

(65) Prior Publication Data
US 2017/0121395 A1     May 4, 2017

Related U.S. Application Data

(60) Provisional application No. 62/249,868, filed on Nov. 2, 2015.

(51) Int. Cl.

| | | |
|---|---|---|
| C07K 16/10 | (2006.01) |
| A61K 45/06 | (2006.01) |
| G01N 33/569 | (2006.01) |
| A61K 39/42 | (2006.01) |
| G01N 33/573 | (2006.01) |
| C07K 16/40 | (2006.01) |
| A61P 31/12 | (2006.01) |
| A61K 39/00 | (2006.01) |

(52) U.S. Cl.
CPC ............ *A61K 45/06* (2013.01); *A61K 39/42* (2013.01); *A61P 31/12* (2018.01); *C07K 16/1045* (2013.01); *C07K 16/40* (2013.01); *G01N 33/56983* (2013.01); *G01N 33/573* (2013.01); *A61K 2039/505* (2013.01); *C07K 2317/22* (2013.01); *C07K 2317/34* (2013.01); *C07K 2317/569* (2013.01); *C07K 2317/92* (2013.01); *G01N 2333/08* (2013.01); *G01N 2333/9128* (2013.01); *G01N 2469/10* (2013.01)

(58) Field of Classification Search
CPC .................. C07K 16/1054; C07K 2317/569
See application file for complete search history.

(56) References Cited

U.S. PATENT DOCUMENTS

| 5,004,697 | A | 4/1991 | Pardridge |
|---|---|---|---|
| 7,638,122 | B2 | 12/2009 | Yu et al. |
| 8,703,131 | B2 | 4/2014 | Beirnaert |
| 8,715,659 | B2 | 5/2014 | Muruganandam et al. |
| 9,067,991 | B2 | 6/2015 | Beirnaert |
| 2004/0052762 | A1 | 3/2004 | Yu et al. |
| 2005/0226863 | A1 | 10/2005 | Colby et al. |
| 2005/0255113 | A1 | 11/2005 | Huston et al. |
| 2005/0272107 | A1 | 12/2005 | Rabbitts et al. |
| 2006/0034845 | A1 | 2/2006 | Silence et al. |
| 2007/0077249 | A1 | 4/2007 | Silence et al. |
| 2009/0022721 | A1 | 1/2009 | Silence et al. |
| 2009/0238829 | A1 | 9/2009 | Silence et al. |
| 2010/0021459 | A1 | 1/2010 | Silence et al. |
| 2010/0143371 | A1 | 6/2010 | Zhu |
| 2011/0027281 | A1 | 2/2011 | Silence et al. |
| 2011/0195509 | A1 | 8/2011 | Pardoll |
| 2011/0250211 | A1 | 10/2011 | Lafaye et al. |
| 2012/0202977 | A1 | 8/2012 | Silence et al. |
| 2013/0177979 | A1 | 7/2013 | Turkson |
| 2014/0335101 | A1 | 11/2014 | Beirnaert |
| 2016/0115226 | A1 | 4/2016 | Singh |
| 2016/0115244 | A1 | 4/2016 | Singh |
| 2016/0115247 | A1 | 4/2016 | Singh |

FOREIGN PATENT DOCUMENTS

| WO | 200178785 A2 | 10/2001 |
|---|---|---|
| WO | 2004041862 A2 | 5/2004 |
| WO | 2009004495 A2 | 1/2009 |
| WO | 2011051327 A2 | 5/2011 |
| WO | 2011163423 A2 | 12/2011 |
| WO | 2015031837 A1 | 3/2015 |
| WO | 2015071856 A1 | 5/2015 |
| WO | 2015071857 A1 | 5/2015 |
| WO | 2015114538 A1 | 8/2015 |
| WO | 2016065323 A2 | 4/2016 |

OTHER PUBLICATIONS

Pellis, M., et al., 2012, A bacterial-two-hybrid selection system for one-step isolation of intracellularly functional nanobodies, Arch. Biochem. Biophy. 526:114-123.*

Koller, G., et al., 1995, Laboratory-scale production and purification of recombinant HIV-1 reverse transcriptase, J. Chromatog. B, 664:107-118.*

Wu, Y., et al., Dec. 2017, Single-domain antibodies as therapeutics against human viral diseases, Front. Immunol. 8(Article 1802):1-13.*

Steeland, S., et al., Jul. 2016, Nanobodies as therapeutics: big opportunities for small antibodies, Drug Discovery Today 21(7):1076-1113.*

(Continued)

*Primary Examiner* — Jeffrey S Parkin

(74) *Attorney, Agent, or Firm* — Laura M. Lloyd; Matrix Law Group, LLP

(57) ABSTRACT

This invention provides compositions and methods to treat a condition or disease without the use of exogenous targeting sequences or chemical compositions. The present invention relates to single-domain antibodies (sdAbs), proteins and polypeptides comprising the sdAbs that are directed against targets that cause a condition or disease. The invention also includes nucleic acids encoding the sdAbs, proteins and polypeptides, and compositions comprising the sdAbs. The invention includes the use of the compositions, sdAbs, and nucleic acids encoding the sdAbs for prophylactic, therapeutic or diagnostic purposes.

2 Claims, 7 Drawing Sheets

Figure 1:
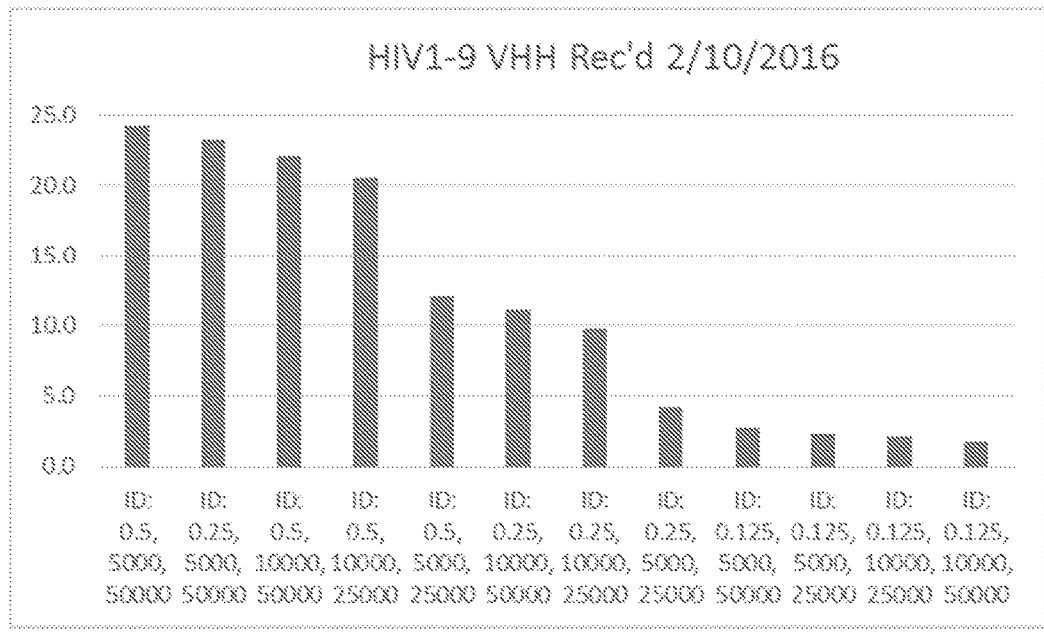

Specification includes a Sequence Listing.

(56) References Cited

OTHER PUBLICATIONS

Imran, M., et al., 2017, Modern biotechnology-based therapeutic approaches against HIV infection (Review), Biomed. Reports 7:504-507.*
Herrera-Carrillo, E., and B. Berkhout, 2015, Potential mechanisms for cell-based gene therapy to treat HIV/AIDS, Expert Opin. Ther. Targets 19(2):245-263.*
Kijanka, M. et al., "Nanobody-based Cancer Therapy of Solid Tumors," Nanomedicine 2015; 10(1):161-174 (26 pages).
Ablynx NV, "Nanobody Advantages," http://www.ablynx.com/en/research-development, Jan. 1, 2013 (2 pages).
Weeks, Don, "Developing Surface Nanobodies Specific to Chlamydomonas Reinhardtii," University of Nebraska—Lincoln, Algal Biomass Summit, Sep. 27, 2012 (32 pages).
Bowman, Tammy, et al., "STATs in Oncogenesis," Oncogene vol. 19, 2000 (pp. 2474-2488).
GLG Pharma, LLC, "A Speciality Pharmaceutical Company . . . developing the next generation of targeted drugs," (22 pages).
Jähnichen, Sven, et al., "CXCR4 Nanobodies (VHH-based single variable domains) Potently Inhibit Chemotaxis and HIV-1 Replication and Mobilize Stem Cells," PNAS, vol. 107, No. 47, Nov. 23, 2010 (pp. 20565-20570).
Jove, Richard, "Preface: STAT Signaling," Oncogene vol. 19, 2000 (pp. 2466-2467).
Kirchhofer, Axel, et al., "Modulation of Protein Properties in Living Cells Using Nanobodies," Nature Structural & Molecular Biology, vol. 17, No. 1, Jan. 2010 (19 pages).
Maussang, David, et al., "Molecular Bases of Disease: Llama-derived Single Variable Domains (Nanobodies) Directed Against Chemokine Receptor CXCR7 Reduce Head and Neck Cancer Growth in Vivo," The Journal of Biological Chemistry, vol. 288, No. 41, Oct. 11, 2013 (pp. 29562-29572).
Turkson et al., "A Novel Platinum Compound Inhibits Constitutive Stat3 Signaling and Induces Cell Cycle Arrest and Apoptosis of Malignant Cells," Journal of Biological Chemistry, vol. 280, No. 38, Sep. 23, 2005, pp. 32979-32988 (10 pages).
Van Impe K. et al., Nanobody Lab, "Use of Camelid Nanobodies as Protein Function Inhibitors in Cancer, Inflammation and Amyloid Diseases, Thus Establishing the Therapeutic of Drug Targets," Universiteit Gent, Department of Biochemistry, Oct. 24, 2012 (2 pages).
Nguyen, Viet Khong, et al., "Camel Heavy-Chain Antibodies: Diverse Germline VHH and Specific Mechanisms Enlarge the Antigen-Binding Repertoire," The EMBO Journal, vol. 19, No. 5, (pp. 921-930).
Rothbauer, Ulrich, et al., "Targeting and Tracing Antigens in Live Cells With Fluorescent Nanobodies," Nature Methods, vol. 3, No. 11, Nov. 2006 (pp. 887-889).
Siddiquee, Khandaker A.Z., "An Oxazole-Based Small-Molecule Stat3 Inhibitor Modulates Stat3 Stability and Processing and Induces Antitumor Cell Effects," ACS Chemical Biology, vol. 2, No. 12 (pp. 787-798).
Siddiquee, Khandaker, "Selective Chemical Probe Inhibitor of Stat3, Identified Through Structure-Based Virtual Screening, Induces Antitumor Activity," PNAS, vol. 104, No. 18, May 1, 2007 (pp. 7391-7396).
Wiecek, Andrew S., "Nanobodies: Going Single-domain," BioTechniques, The International Journal of Life Science Methods, May 4, 2010, (3 pages).
Wolfson, Wendy, "Ablynx Makes Nanobodies from Llama Bodies," Innovations, Chemistry & Biology, vol. 13, Dec. 2006 (pp. 1243-1244).

Li, T. et al., "Cell-penetrating anti-GFAP VHH and corresponding fluorescent fusion protein VHH-GFP spontaneously cross the blood-brain barrier and specifically recognize astrocytes: application to brain imaging." The FASEB Journal, www.fasebj.org., vol. 26, Oct. 2012, pp. 1-11.
Wesolowski, J. et al., "Single domain antibodies: promising experimental and therapeutic tools in infection and immunity," Med. Microbiol. Immunol. (2009) 198:157-174.
Abulrob, A., et al., "The blood-brain barrier transmigrating single domain antibody: mechanisms of transport and antigenic epitopes in human brain endothelial cells," J. Neurochem. (2005) 95, 1201-1214.
Gueorguieva, D., et al., "Identification of single-domain, Bax-specific intrabodies that confer resistance to mammalian cells against oxidative-stress-induced apoptosis," The FASEB Journal, 2006, vol. 20, pp. E2209-E2219.
Nguyen, Viet Khong, et al., "Camel Heavy-Chain Antibodies: Diverse Germline VHH and Specific Mechanisms Enlarge the Antigen-Binding Repertoire," The EMBO Journal, vol. 19, No. 5, 2000, (pp. 921-930).
Roth et al., "Prognosis Role of KRAS and BRAF in Stage II and II Resected Colon Cancer: Results of the Translational Study on the PETACC-3, EORTC 40993, SAKK 60-00 Trial," Journal of Clinical Oncology, vol. 28, No. 3, Jan. 20, 2010, pp. 466-474.
Siddiquee, Khandaker A.Z., "An Oxazole-Based Small-Molecule Stat3 Inhibitor Modulates Stat3 Stability and Processing and Induces Antitumor Cell Effects," ACS Chemical Biology, vol. 2, No. 12, Dec. 21, 2007 (pp. 787-798).
Sommer et al., Constitutively Active Mutant gp130 Receptor Protein from Inflammatory Hepatocellular Adenoma Is Inhibited by an Anti-gp130 Antibody That Specifically Neutralizes Interleukin 11 Signaling, J. Biol. Chem., Apr. 20, 2012, vol. 287, No. 17, pp. 13743-13751.
Tanaka et al., "Single Domain Intracellular Antibodies: A Minimal Fragment for Direct In Vivo Selection of Antigen-specific Intrabodies," J. Mol. Biol., 331:1109-1120, 2003.
Tanaka et al., "Tumour prevention by a single antibody domain targeting the interaction of signal transduction proteins with RAS," The EMBO Journal, 26:3250-3259, 2007.
USPTO, Restriction Requirement and Non-Final Office Action on the Merits issued in related U.S. Appl. No. 14/922,081 dated Feb. 25, 2016 (26 pages).
USPTO, Final Office Action on the Merits issued in related U.S. Appl. No. 14/922,081 dated Sep. 6, 2016 (16 pages).
USPTO, Non-Final Office Action on the Merits issued in related U.S. Appl. No. 14/922,093 dated Jun. 27, 2016 (25 pages).
USPTO, Non-Final Office Action on the Merits issued in related U.S. Appl. No. 14/922,098 dated Apr. 18, 2016 (23 pages).
USPTO, Non-Final Office Action on the Merits issued in related U.S. Appl. No. 14/922,100 dated Jun. 17, 2016 (18 pages).
USPTO, International Search Report (ISR) and Written Opinion issued by the International Searching Authority/US in related International Patent Application No. PCT/US2015/57223 dated Apr. 22, 2016.
USPTO, International Preliminary Report on Patentability (IPRP) issued by the International Searching Authority/US in related International Patent Application No. PCT/US2015/57223 dated Aug. 12, 2016.
Muyldermans S., Single domain camel antibodies: current status. J. Biotechnol. Jun. 2001; 74(4):277-302.
Rudikoff et al., Single amino acid substitution altering antigen-binding specificity. Proc. Natl. Acad. Sci. USA Mar. 1982, 79(6):1979-83.
Single-domain antibody. (May 12, 2016). In Wikipedia, The Free Encyclopedia. Retrieved 21:22, Jun. 20, 2016, from https://en.wikipedia.org/w/index.php?title=Single-domain_antibody&oldid=719821342.

* cited by examiner

FIG. 5

FIG. 6

SEQUENCE LISTING

```
<160> NUMBER OF SEQ ID NOS: 56

<210> SEQ ID NO 1
<211> LENGTH: 259
<212> TYPE: PRT
<213> ORGANISM: Human immunodeficiency virus type 1

<400> SEQUENCE: 1

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Ala Glu Leu Glu Glu Gly Lys Ile Ser
        35                  40                  45

Arg Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Ile Pro Leu Asp Glu Asp Phe Arg Lys Tyr Thr
        115                 120                 125

Ala Phe Thr Ile Pro Ser Thr Asn Asn Glu Thr Pro Gly Thr Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Val Asp Asp Leu Tyr Val Gly Ser Asp
            180                 185                 190

Leu Glu Ile Gly Gln His Arg Thr Lys Val Glu Glu Leu Arg Gln His
        195                 200                 205

Leu Trp Arg Trp Gly Phe Tyr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys

<210> SEQ ID NO 2
<211> LENGTH: 372
<212> TYPE: DNA
<213> ORGANISM: Artificial Sequence
<220> FEATURE:
<223> OTHER INFORMATION: Camelid

<400> SEQUENCE: 2
gatgtgcagc tggtggagtc tgggggaggc tcggtgcagg ctggagggtc tctgagactc      60
tcctgtgcag cctctgttta cagctacaac acaaactgca tgggttggtt ccgccaggct     120
```

```
ccagggaagg agcgcgaggg ggtcgcagtt atttatgctg ctggtggatt aacatactat    180
gccgactccg tgaagggccg attcaccatc tcccaggaga atggcaagaa tacggtgtac    240
ctgacgatga accgcctgaa acctgaggac actgccatgt actactgtgc ggcaaagcga    300
tggtgtagta gctggaatcg cggtgaggag tataactact ggggccaggg gacccaggtc    360
accgtctcct ca                                                         372
```

```
<210> SEQ ID NO 3
<211> LENGTH: 399
<212> TYPE: DNA
<213> ORGANISM: Artificial Sequence
<220> FEATURE:
<223> OTHER INFORMATION: Camelid

<400> SEQUENCE: 3
caggtgcagc tggtggagtc tgggggaggc tcggtgcagg ctggagactc tctgagactc     60
tcctgtgcag cctctggaaa cactgccagt aggttctcca tgggctggtt ccgccaggct    120
ccagggaagg agcgcgaggg ggtcgcggct atttctgctg gtggtaggct acatactat     180 gccgactccg tgaagggccg attcaccatc tcccgagaca cgccaagaa cacgctgtat     240 ctggacatga caacctgaa acctgaggac actgccatgt actactgtgc cgcaattagt     300
gaccggatga ctggtattca ggctcttgcg gctctaccca gacttcgccc agaagactac    360
ggtaactggg gccaggggac cctggtcacc gtctcctca                            399
```

```
<210> SEQ ID NO 4
<211> LENGTH: 402
<212> TYPE: DNA
<213> ORGANISM: Artificial Sequence
<220> FEATURE:
<223> OTHER INFORMATION: Camelid

<400> SEQUENCE: 4
gaggtgcagc tggtggagtc tgggggagac tcggtgcagg ctggagggtc tcttcaactc     60
tcctgtaaag cctctggata cacctacaat agtagagtcg atatcagatc tatgggctgg    120
ttccgccagt atccaggaaa ggagcgcgag ggggtcgcta ctattaatat cgtaatagt     180 gtcacatact atgccgactc cgtgaagggc cgattcacca tctcccaaga caacgccaag    240
aacacggtgt atctgcaaat gaacgccctg aaacctgagg acactgccat gtactactgt    300
gcgttgtcag acagattcgc ggcgcaggta cctgccaggt acggaatacg cccctctgac    360
tataactact ggggtgaggg gaccctggtc accgtctcct ca                        402
```

```
<210> SEQ ID NO 5
<211> LENGTH: 402
<212> TYPE: DNA
<213> ORGANISM: Artificial Sequence
<220> FEATURE:
<223> OTHER INFORMATION: Camelid

<400> SEQUENCE: 5
caggtgcagc tggtggagtc tgggggagac tcggtgcagg ctggagggtc tcttcaactc     60
tcctgtaaag cctctggata cacctacaat agtagagtcg atatcagatc tatgggctgg    120
ttccgccagt atccaggaaa ggagcgcgag ggggtcgcta ctattaatat cgtaatagt     180 gtcacatact atgccgactc cgtgaagggc cgattcacca tctcccaaga caacgccaag    240
aacacggtgt atctgcaaat gaacgccctg aaacctgagg acactgccat gtactactgt    300
gcgttgtcag acagattcgc ggcgcaggta cctgccaggt acggaatacg cccctctgac    360
```

```
tataactact ggggccaggg gacccaggtc accgtctcct ca            402

<210> SEQ ID NO 6
<211> LENGTH: 402
<212> TYPE: DNA
<213> ORGANISM: Artificial Sequence
<220> FEATURE:
<223> OTHER INFORMATION: Camelid

<400> SEQUENCE: 6
caggtgcagc tggtggagtc tgggggagac tcggtgcagg ctggagggtc tcttcaactc    60
tcctgtaaag cctctggata cacctacaat agtagagtcg atatcagatc tatgggctgg   120
ttccgccaat atccaggaaa ggagcgcgag ggggtcgcta ctattaatat tcgtaatagt   180
gtcacatact atgccgactc cgtgaagggc cgattcacca tctcccaaga caacgccaag   240
aacacggtgt atctgcaaat gaacgccctg aaacctgagg acactgccat gtactactgt   300
gcgttgtcag acagattcgc ggcgcaggta cctgccaggt acggaatacg ccctctgac   360 tataactact ggggccaggg gaccctggtc accgtctcct ca           402

<210> SEQ ID NO 7
<211> LENGTH: 401
<212> TYPE: DNA
<213> ORGANISM: Artificial Sequence
<220> FEATURE:
<223> OTHER INFORMATION: Camelid

<400> SEQUENCE: 7
aggtgcagct ggtggagtct gggggagact cggtgcaggc tggagggtct cttcaactct    60
cctgtaaagc tctggatac acctacaata gtagagtcga tatcagatct atgggctggt   120
tccgccagta tccaggaaag gagcgcgagg gggtcgctac tattaatatt cgtaatagtg   180
tcacatacta tgccgactcc gtgaagggcc gattccacat ctcccaagac aacgccaaga   240
acacggtgta tctgcaaatg aacgccctga aacctgagga cactgccatg tactactgtg   300
cgttgtcaga cagattcgcg gcgcaggtac ctgccaggta cggaatacgg ccctctgact   360
ataactactg gggccagggg accctggtca ccgtctcctc a            401

<210> SEQ ID NO 8
<211> LENGTH: 402
<212> TYPE: DNA
<213> ORGANISM: Artificial Sequence
<220> FEATURE:
<223> OTHER INFORMATION: Camelid

<400> SEQUENCE: 8
gaggtgcagc tggtggagtc tgggggagac tcggtgcagg ctggagggtc tcttcaactc    60
tcctgtaaag cctctggata cacctacaat agtagagtcg atatcagatc tatgggctgg   120
ttccgccagt atccaggaaa ggagcgcgag ggggtcgcta ctattaatat tcgtaatagt   180
gtcacatact atgccgactc cgtgaagggc cgattcacca tctcccaaga caacgccaag   240
aacacggtgt atctgcaaat gaacgccctg aaacctgagg acactgccat gtactactgt   300
gcgttgtcag acagattcgc ggcgcaggta cctgccaggt acggaatacg ccctctgac   360 tataactact ggggtgaggg gacccaggtc accgtctcct ca           402

<210> SEQ ID NO 9
<211> LENGTH: 402
<212> TYPE: DNA
```

```
<213> ORGANISM: Artificial Sequence
<220> FEATURE:
<223> OTHER INFORMATION: Camelid

<400> SEQUENCE: 9
gaggtgcagc tggtggagtc tgggggagac tcggtgcagg ctggagggtc tcttcaactc     60
tcctgtaaag cctctggata cacctacaat agtagagtcg atatcagatc tatgggctgg    120
ttccgccagt atccaggaaa ggagcgcgag ggggtcgcta ctattaatat tcgtaatagt    180
gtcacatact atgccgactc cgtgaagggc cgattcacca tctcccaaga caacgccaag    240
aacacggtgt atctgcaaat gaacgccctg aaacctgagg acactgccat gtactactgt    300
gcgttgtcag acagattcgc ggcgcaggta cctgccaggt acggaatacg gccctctgac    360
tataactact ggggtgaggg gacccaggtc accgtctcct ca                       402

<210> SEQ ID NO 10
<211> LENGTH: 402
<212> TYPE: DNA
<213> ORGANISM: Artificial Sequence
<220> FEATURE:
<223> OTHER INFORMATION: Camelid

<400> SEQUENCE: 10
gaggtgcagc tggtggagtc tgggggagac tcggtgcagg ctggagggtc tcttcaactc     60
tcctgtaaag cctctggata cacctacaat agtagagtcg atatcagatc tatgggctgg    120
ttccgccagt atccaggaaa ggagcgcgag ggggtcgcta ctattaatat tcgtaatagt    180
gtcacatact atgccgactc cgtgaagggc cgattcacca tctcccaaga caacgccaag    240
aacacggtgt atctgcaaat gaacgccctg aaacctgagg acactgccat gtactactgt    300
gcgttgtcag acagattcgc ggcgcaggta cctgccaggt acggaatacg gccctctgac    360
tataactact ggggtgaggg gacccaggtc actgtctcct ca                       402

<210> SEQ ID NO 11
<211> LENGTH: 402
<212> TYPE: DNA
<213> ORGANISM: Artificial Sequence
<220> FEATURE:
<223> OTHER INFORMATION: Camelid

<400> SEQUENCE: 11
gaggtgcagc tggtggagtc tgggggagac tcggtgcagg ctggagggtc tcttcaactc     60
tcctgtaagg cctctggata cacctacaat agtagagtcg atatcagatc tatgggctgg    120
ttccgccagt atccaggaaa ggagcgcgag ggggtcgcta ccattaatat tcgtaatagt    180
gtcacatact atgccgactc cgtgaagggc cgattcacca tctcccaaga caacgctaag    240
aacacggtgt atctgcaaat gaacgccctg aaacctgagg acactgccat gtactactgt    300
gcgttgtcag acagattcgc ggcgcaggta cctgccaggt acggaatacg gccctctgac    360
tataactact ggggtgaggg gacccaggtc accgtctcct ca                       402

<210> SEQ ID NO 12
<211> LENGTH: 402
<212> TYPE: DNA
<213> ORGANISM: Artificial Sequence
<220> FEATURE:
<223> OTHER INFORMATION: Camelid

<400> SEQUENCE: 12
gaggtgcagc tggtggagtc tgggggagac tcggtgcagg ctggagggtc tcttcaactc     60
```

```
tcctgtaaag cctctggata cacctacaat agtagagtcg atatcagatc tatgggctgg      120
ttccgccagt atccaggaaa ggagcgcgag ggggtcgcta ctattaatat tcgtaatagt      180
gtcacatact atgccgactc cgtgaagggc cgattcacca tctcccaaga caacgccaag      240
aacacggtgt atctgcaaat gaacgccctg aaacctgagg acactgccat gtactactgt      300
gcgttgtcag acagattcgc agcgcaggta cctgccaggt acggaatacg gccctctgac      360
tataactact ggggtgaggg gacccaggtc accgtctcct ca                        402
```

<210> SEQ ID NO 13
<211> LENGTH: 402
<212> TYPE: DNA
<213> ORGANISM: Artificial Sequence
<220> FEATURE:
<223> OTHER INFORMATION: Camelid

<400> SEQUENCE: 13

```
gaggtgcagc tggtggagtc tgggggagac tcagtgcagg ctggagggtc tcttcaactc       60
tcctgtaaag cctctggata cacctacaat agtagagtcg atatcagatc tatgggctgg      120
ttccgccagt atccaggaaa ggagcgcgag ggggtcgcta ctattaatat tcgtaatagt      180
gtcacatact atgccgactc cgtgaagggc cgattcacca tctcccaaga caacgccaag      240
aacacggtgt atctgcaaat gaacgccctg aaacctgagg acactgccat gtactactgt      300
gcgttgtcag acagattcgc ggcgcaggta cctgccaggt acggaatacg gccctctgac      360
tataactact ggggtgaggg gacccaggtc accgtctcct ca                        402
```

<210> SEQ ID NO 14
<211> LENGTH: 402
<212> TYPE: DNA
<213> ORGANISM: Artificial Sequence
<220> FEATURE:
<223> OTHER INFORMATION: Camelid

<400> SEQUENCE: 14

```
gaggtgcagc tggtggagtc tgggggagac tcggtgcagg ctggagggtc tcttcaactc       60
tcctgtaaag cctctggata cacctacaat agtagagtcg atatcagatc tatgggctgg      120
ttccgccagt atccaggaaa ggagcgcgcag ggggtcgcta ctattaatat tcgtaatagt     180
gtcacatact atgccgactc cgtgaagggc cgattcacca tctcccaaga caacgccaag      240
aacacggtgt atctgcaaat gaacgccctg aaacctgagg acactgccat gtactactgt      300
gcgttgtcag acagattcgc ggcgcaggta cctgccaggt acggaatacg gccctctgac      360
tataactact ggggtgaggg gacccaggtc accgtctcct ca                        402
```

<210> SEQ ID NO 15
<211> LENGTH: 372
<212> TYPE: DNA
<213> ORGANISM: Artificial Sequence
<220> FEATURE:
<223> OTHER INFORMATION: Camelid

<400> SEQUENCE: 15

```
gaggtgcagc tggtggagtc tgggggaggc tcggtgcagg ctggagggtc tctgagactc       60
tcctgtgcag cctctgttta cagctacaac acaaactgca tgggttggtt ccgccaggct      120
ccagggaagg agcgcgaggg ggtcgcagtt atttatgctg ctggtggatt aacatactat      180
gccgactccg tgaagggccg attcaccatc tcccaggaga atgcaagaa cacggtgtac      240
```

| | |
|---|---|
| ctgacgatga accgcctgaa acctgaggac actgccatgt actactgtgc ggcaaagcga | 300 |
| tggtgtagta gctggaatcg cggtgaggag tataactact ggggccaggg gacccaggtc | 360 |
| actgtctcct ca | 372 |

<210> SEQ ID NO 16
<211> LENGTH: 384
<212> TYPE: DNA
<213> ORGANISM: Artificial Sequence
<220> FEATURE:
<223> OTHER INFORMATION: Camelid

<400> SEQUENCE: 16

| | |
|---|---|
| caggtgcagc tggtggagtc tgggggaggc tcggtgcagg ctggagggtc tctgagactc | 60 |
| tcctgtgcag cctctggaaa cacctacagt agtagctact gcatgggctg gttccgccag | 120 |
| gctccaggga aggaccgcga ggggtcgcg cgtatttcca ctcgaagtgg taccacatac | 180 |
| tatgccgact ccgtgaaggg ccgattcacc atttcccgtg acaacgccaa gaacacggtg | 240 |
| tatctgcaaa tgaacagcct gaaacctgaa gacgctgcca tgtactactg tgcggcagcc | 300 |
| caggggggtg cctgcatttc gtttacttcg ttcgcgaaga atttcgtgta ccggggccag | 360 |
| gggaccctgg tcactgtctc ctca | 384 |

<210> SEQ ID NO 17
<211> LENGTH: 402
<212> TYPE: DNA
<213> ORGANISM: Artificial Sequence
<220> FEATURE:
<223> OTHER INFORMATION: Camelid

<400> SEQUENCE: 17

| | |
|---|---|
| gaggtgcagc tggtggagtc tgggggagac tcggtgcagg ctggagggtc tcttcaactc | 60 |
| tcctgtaaag cctctggata cacctacaat agtagagtcg atatcagatc tatgggctgg | 120 |
| ttccgccagt atccaggaaa ggagcgcgag ggggtcgcta ctattaatat tcgtaatagt | 180 |
| gtcacatact atgccgactc cgtgaagggc cgattcacca tctcccaaga caacgccaag | 240 |
| aacacggtgt atctgcaaat gaacgccctg aaacctgagg acactgccat gtactactgt | 300 |
| gcgttgtcag acagattcgc ggcgcaggta cctgccaggt acggaatacg gtcctctgac | 360 |
| tataactact ggggtgaggg gaccctggtc accgtctcct ca | 402 |

<210> SEQ ID NO 18
<211> LENGTH: 402
<212> TYPE: DNA
<213> ORGANISM: Artificial Sequence
<220> FEATURE:
<223> OTHER INFORMATION: Camelid

<400> SEQUENCE: 18

| | |
|---|---|
| gaggtgcagc tggtggagtc tgggggagac tcggtgcagg ctggagggtc tcttcaactc | 60 |
| tcctgtaaag cctctggata cacctacaat agtagagtcg atatcagatc tatgggctgg | 120 |
| ttccgccagt atccaggaaa ggagcgcgag ggggtcgcta ctattaatat tcgtaatagt | 180 |
| gtcacatact atgccgactc cgtgaagggc cgattcacca tctcccaaga caacgccaag | 240 |
| aacacggtgt atctgcaaat gaacgccctg aaacctgagg acactgccat gtactactgt | 300 |
| gcgttgtcag acagattcgc ggcgcaggta cctgccaggt acggaatacg gtcctctgac | 360 |
| tataactact ggggtgaggg gaccctggtc accgtctcct ca | 402 |

<210> SEQ ID NO 19
<211> LENGTH: 402
<212> TYPE: DNA
<213> ORGANISM: Artificial Sequence
<220> FEATURE:
<223> OTHER INFORMATION: Camelid

<400> SEQUENCE: 19

```
caggtgcagc tggtggagtc tgggggagac tcggtgcagg ctggagggtc tcttcaactc      60
tcctgtaaag cctctggata cacctacaat agtagagtcg atatcagatc tatgggctgg     120
ttccgccagt atccaggaaa ggagcgcgag ggggtcgcta ctattaatat tcgtaatagt     180
gtcacatact atgccgactc cgtgaagggc cgattcacca tctcccaaga caacgccaag     240
aacacggtgt atctgcaaat gaacgccctg aaacctgagg acactgccat gtactactgt     300
gcgttgtcag acagattcgc ggcgcaggta cctgccaggt acggaatacg gccctctgac     360
tataactact ggggtgaggg gacccaggtc actgtctcct ca                        402
```

<210> SEQ ID NO 20
<211> LENGTH: 402
<212> TYPE: DNA
<213> ORGANISM: Artificial Sequence
<220> FEATURE:
<223> OTHER INFORMATION: Camelid

<400> SEQUENCE: 20

```
caggtgcagc tggtggagtc tgggggagac tcggtgcagg ctggagggtc tcttcaactc      60
tcctgtaaag cctctggata cacctacaat agtagagtcg atatcagatc tatgggctgg     120
ttccgccagt atccaggaaa ggagcgcgag ggggtcgcta ctattaatat tcgtaatagt     180
gtcacatact atgccgactc cgtgaagggc cgattcacca tctcccaaga caacgccaag     240
aacacggtgt atctgcaaat gaacgccctg aaacctgagg acactgccat gtactactgt     300
gcgttgtcag acagattcgc ggcgcaggta cctgccaggt acggaatacg gccctctgac     360
tataactact ggggtgaggg gacccaggtc accgtctcct ca                        402
```

<210> SEQ ID NO 21
<211> LENGTH: 402
<212> TYPE: DNA
<213> ORGANISM: Artificial Sequence
<220> FEATURE:
<223> OTHER INFORMATION: Camelid

<400> SEQUENCE: 21

```
catgtgcagc tggtggagtc tgggggagac tcggtgcagg ctggagggtc tcttcaactc      60
tcctgtaaag cctctggata cacctacaat agtagagtcg atatcagatc tatgggctgg     120
ttccgccagt atccaggaaa ggagcgcgag ggggtcgcta ctattaatat tcgtaatagt     180
gtcacatact atgccgactc cgtgaagggc cgattcacca tctcccaaga caacgccaag     240
aacacggtgt atctgcaaat gaacgccctg aaacctgagg acactgccat gtactactgt     300
gcgttgtcag acagattcgc ggcgcaggta cctgccaggt acggaatacg gccctctgac     360
tataactact ggggtgaggg gaccctggtc accgtctcct ca                        402
```

<210> SEQ ID NO 22
<211> LENGTH: 402
<212> TYPE: DNA
<213> ORGANISM: Artificial Sequence
<220> FEATURE:
<223> OTHER INFORMATION: Camelid

<400> SEQUENCE: 22

```
gaggtgcagc tggtggagtc tgggggagac tcggtgcagg ctggagggtc tcttcaactc      60
tcctgtaaag cctctggata cacctacaat agtagagtcg atatcagatc tatgggctgg     120
ttccgccagt atccaggaaa ggagcgcgag ggggtcgcta ctattaatat tcgtaatagt     180
gtcacatact atgccaactc cgtgaagggc cgattcacca tctcccaaga caacgccaag     240
aacacggtgt atctgcaaat gaacgccctg aaacctgagg acactgccat gtactactgt     300
gcgttgtcag acagattcgc ggcgcaggta cctgccaggt acggaatacg gccctctgac     360
tatgactact ggggtgaggg gaccctggtc accgtctcct ca                        402
```

<210> SEQ ID NO 23
<211> LENGTH: 402
<212> TYPE: DNA
<213> ORGANISM: Artificial Sequence
<220> FEATURE:
<223> OTHER INFORMATION: Camelid

<400> SEQUENCE: 23

```
gaggtgcagc tggtggagtc tgggggagac tcggtgcagg ctggagggtc tcttcaactc      60
tcctgtaaag cctctggata cacctacaat agtagagtcg atatcagatc tatgggctgg     120
ttccgccagt atccaggaaa ggagcgcgag ggggtcgcta ctattaatat tcgtaatagt     180
gtcacatact atgccgactc cgtgaagggc cgattcacca tctcccaaga caacgccaag     240
aacacggtgt atctgcaaat ggacgccctg aaacctgagg acactgccat gtactactgt     300
gcgttgtcag acagattcgc ggcgcaggta cctgccaggt acggaatacg gccctctgac     360
tataactact ggggtgaggg gacccaggtc accgtctcct ca                        402
```

<210> SEQ ID NO 24
<211> LENGTH: 402
<212> TYPE: DNA
<213> ORGANISM: Artificial Sequence
<220> FEATURE:
<223> OTHER INFORMATION: Camelid

<400> SEQUENCE: 24

```
gaggtgcagc tggtggagtc tgggggagac tcggtgcagg ctggagggtc tcttcaactc      60
tcctgtaagg cctctggata cacctacaat agtagagtcg atatcagatc tgtgggctgg     120
ttccgccagt atccaggaaa ggagcgcgag ggggtcgcta ctattaatat tcgtaatagt     180
gtcacatact atgccgactc cgtgaagggc cgattcacca tctcccaaga caacgccaag     240
aacacggtgt atctgcaaat gaacgccctg aaacctgagg acactgccat gtactactgt     300
gcgttgtcag acagattcgc ggcgcaggta cctgccaggt acggaatacg gccctctgac     360
tataactact ggggtgaggg gacccaggtc accgtctcct ca                        402
```

<210> SEQ ID NO 25
<211> LENGTH: 124
<212> TYPE: PRT
<213> ORGANISM: Artificial Sequence
<220> FEATURE:
<223> OTHER INFORMATION: Camelid

<400> SEQUENCE: 25

```
Asp Val Gln Leu Val Glu Ser Gly Gly Gly Ser Val Gln Ala Gly Gly
1               5                   10                  15

Ser Leu Arg Leu Ser Cys Ala Ala Ser Val Tyr Ser Tyr Asn Thr Asn
            20                  25                  30
```

Cys Met Gly Trp Phe Arg Gln Ala Pro Gly Lys Glu Arg Glu Gly Val
         35                  40                  45

Ala Val Ile Tyr Ala Ala Gly Gly Leu Thr Tyr Tyr Ala Asp Ser Val
     50                  55                  60

Lys Gly Arg Phe Thr Ile Ser Gln Glu Asn Gly Lys Asn Thr Val Tyr
65                  70                  75                  80

Leu Thr Met Asn Arg Leu Lys Pro Glu Asp Thr Ala Met Tyr Tyr Cys
                 85                  90                  95

Ala Ala Lys Arg Trp Cys Ser Ser Trp Asn Arg Gly Glu Glu Tyr Asn
                100                 105                 110

Tyr Trp Gly Gln Gly Thr Gln Val Thr Val Ser Ser
         115                 120

<210> SEQ ID NO 26
<211> LENGTH: 133
<212> TYPE: PRT
<213> ORGANISM: Artificial Sequence
<220> FEATURE:
<223> OTHER INFORMATION: Camelid

<400> SEQUENCE: 26

Gln Val Gln Leu Val Glu Ser Gly Gly Gly Ser Val Gln Ala Gly Asp
1               5                   10                  15

Ser Leu Arg Leu Ser Cys Ala Ala Ser Gly Asn Thr Ala Ser Arg Phe
             20                  25                  30

Ser Met Gly Trp Phe Arg Gln Ala Pro Gly Lys Glu Arg Glu Gly Val
         35                  40                  45

Ala Ala Ile Ser Ala Gly Gly Arg Leu Thr Tyr Tyr Ala Asp Ser Val
     50                  55                  60

Lys Gly Arg Phe Thr Ile Ser Arg Asp Asn Ala Lys Asn Thr Leu Tyr
65                  70                  75                  80

Leu Asp Met Asn Asn Leu Lys Pro Glu Asp Thr Ala Met Tyr Tyr Cys
                 85                  90                  95

Ala Ala Ile Ser Asp Arg Met Thr Gly Ile Gln Ala Leu Ala Ala Leu
                100                 105                 110

Pro Arg Leu Arg Pro Glu Asp Tyr Gly Asn Trp Gly Gln Gly Thr Leu
         115                 120                 125

Val Thr Val Ser Ser
        130

<210> SEQ ID NO 27
<211> LENGTH: 124
<212> TYPE: PRT
<213> ORGANISM: Artificial Sequence
<220> FEATURE:
<223> OTHER INFORMATION: Camelid

<400> SEQUENCE: 27

Glu Val Gln Leu Val Glu Ser Gly Gly Gly Ser Val Gln Ala Gly Gly
1               5                   10                  15

Ser Leu Arg Leu Ser Cys Ala Ala Ser Val Tyr Ser Tyr Asn Thr Asn
             20                  25                  30

Cys Met Gly Trp Phe Arg Gln Ala Pro Gly Lys Glu Arg Glu Gly Val
         35                  40                  45

Ala Val Ile Tyr Ala Ala Gly Gly Leu Thr Tyr Tyr Ala Asp Ser Val
     50                  55                  60

Lys Gly Arg Phe Thr Ile Ser Gln Glu Asn Gly Lys Asn Thr Val Tyr

```
            65                  70                  75                  80
Leu Thr Met Asn Arg Leu Lys Pro Glu Asp Thr Ala Met Tyr Tyr Cys
                85                  90                  95

Ala Ala Lys Arg Trp Cys Ser Ser Trp Asn Arg Gly Glu Glu Tyr Asn
            100                 105                 110

Tyr Trp Gly Gln Gly Thr Gln Val Thr Val Ser Ser
        115                 120

<210> SEQ ID NO 28
<211> LENGTH: 128
<212> TYPE: PRT
<213> ORGANISM: Artificial Sequence
<220> FEATURE:
<223> OTHER INFORMATION: Camelid

<400> SEQUENCE: 28

Gln Val Gln Leu Val Glu Ser Gly Gly Gly Ser Val Gln Ala Gly Gly
1               5                   10                  15

Ser Leu Arg Leu Ser Cys Ala Ala Ser Gly Asn Thr Tyr Ser Ser Ser
            20                  25                  30

Tyr Cys Met Gly Trp Phe Arg Gln Ala Pro Gly Lys Asp Arg Glu Gly
        35                  40                  45

Val Ala Arg Ile Phe Thr Arg Ser Gly Thr Thr Tyr Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Ala Ala Met Tyr Tyr
                85                  90                  95

Cys Ala Ala Ala Gln Gly Gly Ala Cys Ile Ser Phe Thr Ser Phe Ala
            100                 105                 110

Lys Asn Phe Val Tyr Arg Gly Gln Gly Thr Leu Val Thr Val Ser Ser
        115                 120                 125

<210> SEQ ID NO 29
<211> LENGTH: 124
<212> TYPE: PRT
<213> ORGANISM: Artificial Sequence
<220> FEATURE:
<223> OTHER INFORMATION: Camelid

<400> SEQUENCE: 29

Glu Val Gln Leu Gly Glu Ser Gly Gly Gly Ser Val Gln Ala Gly Gly
1               5                   10                  15

Ser Leu Arg Leu Ser Cys Ala Ala Ser Val Tyr Ser Tyr Thr Thr Asn
            20                  25                  30

Cys Met Gly Trp Phe Arg Gln Ala Pro Gly Lys Glu Arg Glu Gly Val
        35                  40                  45

Ala Val Ile Tyr Ser Ala Gly Gly Leu Thr Tyr Tyr Ala Asp Ser Val
    50                  55                  60

Lys Gly Arg Phe Thr Ile Ser Gln Asp Asn Gly Lys Asn Thr Val Tyr
65                  70                  75                  80

Leu Thr Met Asn Arg Leu Lys Pro Glu Asp Thr Ala Met Tyr Tyr Cys
                85                  90                  95

Ala Ala Lys Arg Trp Cys Ser Ser Trp Asn Arg Gly Glu Glu Tyr Asn
            100                 105                 110

Tyr Trp Gly Gln Gly Thr Gln Val Thr Val Ser Ser
        115                 120
```

<210> SEQ ID NO 30
<211> LENGTH: 124
<212> TYPE: PRT
<213> ORGANISM: Artificial Sequence
<220> FEATURE:
<223> OTHER INFORMATION: Camelid

<400> SEQUENCE: 30

Gln Val Gln Leu Val Glu Ser Gly Gly Gly Ser Val Gln Ala Gly Gly
1               5                   10                  15

Ser Leu Arg Leu Ser Cys Ala Ala Ser Val Tyr Ser Tyr Asn Thr Asn
            20                  25                  30

Cys Met Gly Trp Phe Arg Gln Ala Pro Gly Lys Glu Arg Glu Gly Ala
        35                  40                  45

Ala Val Ile Tyr Ala Ala Gly Leu Thr Tyr Ala Asp Ser Val
    50                  55                  60

Lys Gly Arg Phe Thr Ile Ser Gln Glu Asn Gly Lys Asn Thr Val Tyr
65                  70                  75                  80

Leu Thr Met Asn Arg Leu Lys Pro Glu Asp Thr Ala Met Tyr Tyr Cys
                85                  90                  95

Ala Ala Lys Arg Trp Cys Ser Ser Trp Asn Arg Gly Glu Glu Tyr Asn
            100                 105                 110

Tyr Trp Gly Gln Gly Thr Gln Val Thr Val Ser Ser
        115                 120

<210> SEQ ID NO 31
<211> LENGTH: 134
<212> TYPE: PRT
<213> ORGANISM: Artificial Sequence
<220> FEATURE:
<223> OTHER INFORMATION: Camelid

<400> SEQUENCE: 31

Glu Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
            20                  25                  30

Val Asp Ile Arg Ser Met Gly Trp Phe Arg Gln Tyr Pro Gly Lys Glu
        35                  40                  45

Arg Glu Gly Val Ala Thr Ile Asn Ile Arg Asn Ser Val Thr Tyr Tyr
    50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                85                  90                  95

Met Tyr Tyr Cys Ala Leu Ser Asp Arg Phe Ala Ala Gln Val Pro Ala
            100                 105                 110

Arg Tyr Gly Ile Arg Pro Ser Asp Tyr Asn Tyr Trp Gly Glu Gly Thr
        115                 120                 125

Gln Val Thr Val Ser Ser
    130

<210> SEQ ID NO 32
<211> LENGTH: 134
<212> TYPE: PRT
<213> ORGANISM: Artificial Sequence
<220> FEATURE:
<223> OTHER INFORMATION: Camelid

```
<400> SEQUENCE: 32

His Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
            20                  25                  30

Val Asp Ile Arg Ser Met Gly Trp Phe Arg Gln Tyr Pro Gly Lys Glu
        35                  40                  45

Arg Glu Gly Val Ala Thr Ile Asn Ile Arg Asn Ser Val Thr Tyr Tyr
    50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                85                  90                  95

Met Tyr Tyr Cys Ala Leu Ser Asp Arg Phe Ala Ala Gln Val Pro Ala
            100                 105                 110

Arg Tyr Gly Ile Arg Pro Ser Asp Tyr Asn Tyr Trp Gly Glu Gly Thr
        115                 120                 125

Leu Val Thr Val Ser Ser
    130

<210> SEQ ID NO 33
<211> LENGTH: 134
<212> TYPE: PRT
<213> ORGANISM: Artificial Sequence
<220> FEATURE:
<223> OTHER INFORMATION: Camelid

<400> SEQUENCE: 33

Gln Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
            20                  25                  30

Val Asp Ile Arg Ser Met Gly Trp Phe Arg Gln Tyr Pro Gly Lys Glu
        35                  40                  45

Arg Glu Gly Val Ala Thr Ile Asn Ile Arg Asn Ser Val Thr Tyr Tyr
    50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                85                  90                  95

Met Tyr Tyr Cys Ala Leu Ser Asp Arg Phe Ala Ala Gln Val Pro Ala
            100                 105                 110

Arg Tyr Gly Ile Arg Pro Ser Asp Tyr Asn Tyr Trp Gly Gln Gly Thr
        115                 120                 125

Leu Val Thr Val Ser Ser
    130

<210> SEQ ID NO 34
<211> LENGTH: 134
<212> TYPE: PRT
<213> ORGANISM: Artificial Sequence
<220> FEATURE:
<223> OTHER INFORMATION: Camelid

<400> SEQUENCE: 34

Glu Val Gln Leu Val Glu Ser Gly Gly Asp Ser Val Gln Ala Gly Gly
1               5                   10                  15
```

Ser Leu Gln Leu Ser Cys Lys Ala Ser Gly Tyr Thr Tyr Asn Ser Arg
             20                  25                  30

Val Asp Ile Arg Ser Met Gly Trp Phe Arg Gln Tyr Pro Gly Lys Glu
         35                  40                  45

Arg Glu Gly Val Ala Thr Ile Asn Ile Arg Asn Ser Val Thr Tyr Tyr
     50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                 85                  90                  95

Met Tyr Tyr Cys Ala Leu Ser Asp Arg Phe Ala Ala Gln Val Pro Ala
            100                 105                 110

Arg Tyr Gly Ile Arg Pro Ser Asp Tyr Asn Tyr Trp Gly Glu Gly Thr
        115                 120                 125

Leu Val Thr Val Ser Ser
        130

<210> SEQ ID NO 35
<211> LENGTH: 134
<212> TYPE: PRT
<213> ORGANISM: Artificial Sequence
<220> FEATURE:
<223> OTHER INFORMATION: Camelid

<400> SEQUENCE: 35

Gln Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
             20                  25                  30

Val Asp Ile Arg Ser Met Gly Trp Phe Arg Gln Tyr Pro Gly Lys Glu
         35                  40                  45

Arg Glu Gly Val Ala Thr Ile Asn Ile Arg Asn Ser Val Thr Tyr Tyr
     50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                 85                  90                  95

Met Tyr Tyr Cys Ala Leu Ser Asp Arg Phe Ala Ala Gln Val Pro Ala
            100                 105                 110

Arg Tyr Gly Ile Arg Pro Ser Asp Tyr Asn Tyr Trp Gly Gln Gly Thr
        115                 120                 125

Gln Val Thr Val Ser Ser
        130

<210> SEQ ID NO 36
<211> LENGTH: 134
<212> TYPE: PRT
<213> ORGANISM: Artificial Sequence
<220> FEATURE:
<223> OTHER INFORMATION: Camelid

<400> SEQUENCE: 36

Gln Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
             20                  25                  30

Val Asp Ile Arg Ser Met Gly Trp Phe Arg Gln Tyr Pro Gly Lys Glu
         35                  40                  45

```
Arg Glu Gly Val Ala Thr Ile Asn Ile Arg Asn Ser Val Thr Tyr Tyr
        50                  55                  60

Ala Asp Ser Val Lys Gly Arg Phe Thr Ile Ser Gln Asp Asn Ala Lys
 65                  70                  75                  80

Asn Thr Val Tyr Leu Gln Met Asn Ala Leu Lys Pro Glu Asp Thr Ala
                85                  90                  95

Met Tyr Tyr Cys Ala Leu Ser Asp Arg Phe Ala Ala Gln Val Pro Ala
                100                 105                 110

Arg Tyr Gly Ile Arg Pro Ser Asp Tyr Asn Tyr Trp Gly Glu Gly Thr
            115                 120                 125

Gln Val Thr Val Ser Ser
        130

<210> SEQ ID NO 37
<211> LENGTH: 134
<212> TYPE: PRT
<213> ORGANISM: Artificial Sequence
<220> FEATURE:
<223> OTHER INFORMATION: Camelid

<400> SEQUENCE: 37

Glu Val Gln Leu Val Glu Ser Gly Gly Asp Ser Val Gln Ala Gly Gly
 1               5                  10                  15

Ser Leu Gln Leu Ser Cys Lys Ala Ser Gly Tyr Thr Tyr Asn Ser Arg
                20                  25                  30

Val Asp Ile Arg Ser Met Gly Trp Phe Arg Gln Tyr Pro Gly Lys Glu
            35                  40                  45

Arg Glu Gly Val Ala Thr Ile Asn Ile Arg Asn Ser Val Thr Tyr Tyr
        50                  55                  60

Ala Asp Ser Val Lys Gly Arg Phe Thr Ile Ser Gln Asp Asn Ala Lys
 65                  70                  75                  80

Asn Thr Val Tyr Leu Gln Met Asn Ala Leu Lys Pro Glu Asp Thr Ala
                85                  90                  95

Met Tyr Tyr Cys Ala Leu Ser Asp Arg Phe Ala Ala Gln Val Pro Ala
                100                 105                 110

Arg Tyr Gly Ile Arg Ser Ser Asp Tyr Asn Tyr Trp Gly Glu Gly Thr
            115                 120                 125

Leu Val Thr Val Ser Ser
        130

<210> SEQ ID NO 38
<211> LENGTH: 134
<212> TYPE: PRT
<213> ORGANISM: Artificial Sequence
<220> FEATURE:
<223> OTHER INFORMATION: Camelid

<400> SEQUENCE: 38

Glu Val Gln Leu Val Glu Ser Gly Gly Asp Ser Val Gln Ala Gly Gly
 1               5                  10                  15

Ser Leu Gln Leu Ser Cys Lys Ala Ser Gly Tyr Thr Tyr Asn Ser Arg
                20                  25                  30

Val Asp Ile Arg Ser Met Gly Trp Phe Arg Gln Tyr Pro Gly Lys Glu
            35                  40                  45

Arg Glu Gly Val Ala Thr Ile Asn Ile Arg Asn Ser Val Thr Tyr Tyr
        50                  55                  60

Ala Asp Ser Val Lys Gly Arg Phe Thr Ile Ser Gln Asp Asn Ala Lys
```

```
                65                  70                  75                  80
Asn Thr Val Tyr Leu Gln Met Asp Ala Leu Lys Pro Glu Asp Thr Ala
                    85                  90                  95

Met Tyr Tyr Cys Ala Leu Ser Asp Arg Phe Ala Ala Gln Val Pro Ala
                    100                 105                 110

Arg Tyr Gly Ile Arg Pro Ser Asp Tyr Asn Tyr Trp Gly Glu Gly Thr
                    115                 120                 125

Gln Val Thr Val Ser Ser
            130

<210> SEQ ID NO 39
<211> LENGTH: 134
<212> TYPE: PRT
<213> ORGANISM: Artificial Sequence
<220> FEATURE:
<223> OTHER INFORMATION: Camelid

<400> SEQUENCE: 39

His Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
                20                  25                  30

Val Asp Ile Arg Ser Met Gly Trp Phe Arg Gln Tyr Pro Gly Lys Glu
            35                  40                  45

Arg Glu Gly Val Ala Thr Ile Asn Ile Arg Asn Ser Val Thr Tyr Tyr
        50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Gly Asp Thr Ala
                    85                  90                  95

Met Tyr Tyr Cys Ala Leu Ser Asp Arg Phe Ala Ala Gln Val Pro Ala
                    100                 105                 110

Arg Tyr Gly Ile Arg Pro Ser Asp Tyr Asn Tyr Trp Gly Gln Gly Thr
                    115                 120                 125

Leu Val Thr Val Ser Ser
            130

<210> SEQ ID NO 40
<211> LENGTH: 134
<212> TYPE: PRT
<213> ORGANISM: Artificial Sequence
<220> FEATURE:
<223> OTHER INFORMATION: Camelid

<400> SEQUENCE: 40

Glu Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
                20                  25                  30

Val Asp Ile Arg Ser Val Gly Trp Phe Arg Gln Tyr Pro Gly Lys Glu
            35                  40                  45

Arg Glu Gly Val Ala Thr Ile Asn Ile Arg Asn Ser Val Thr Tyr Tyr
        50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                    85                  90                  95
```

```
Met Tyr Tyr Cys Ala Leu Ser Asp Arg Phe Ala Ala Gln Val Pro Ala
            100                 105                 110

Arg Tyr Gly Ile Arg Pro Ser Asp Tyr Asn Tyr Trp Gly Glu Gly Thr
        115                 120                 125

Gln Val Thr Val Ser Ser
        130

<210> SEQ ID NO 41
<211> LENGTH: 134
<212> TYPE: PRT
<213> ORGANISM: Artificial Sequence
<220> FEATURE:
<223> OTHER INFORMATION: Camelid

<400> SEQUENCE: 41

Asp Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
            20                  25                  30

Val Asp Ile Arg Ser Met Gly Trp Phe Arg Gln Tyr Pro Gly Lys Glu
        35                  40                  45

Arg Glu Gly Val Ala Thr Ile Asn Ile Arg Asn Ser Val Thr Tyr Tyr
    50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                85                  90                  95

Met Tyr Tyr Cys Ala Leu Ser Asp Arg Phe Ala Ala Gln Val Pro Ala
            100                 105                 110

Arg Tyr Gly Ile Arg Pro Ser Asp Tyr Asn Tyr Trp Gly Glu Gly Thr
        115                 120                 125

Gln Val Thr Val Ser Ser
        130

<210> SEQ ID NO 42
<211> LENGTH: 134
<212> TYPE: PRT
<213> ORGANISM: Artificial Sequence
<220> FEATURE:
<223> OTHER INFORMATION: Camelid

<400> SEQUENCE: 42

Glu Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
            20                  25                  30

Val Asp Ile Arg Ser Met Gly Trp Phe Arg Gln Tyr Pro Gly Lys Glu
        35                  40                  45

Arg Glu Gly Val Ala Thr Ile Asn Ile Arg Asn Ser Val Thr Tyr Tyr
    50                  55                  60

Ala Asn Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                85                  90                  95

Met Tyr Tyr Cys Ala Leu Ser Asp Arg Phe Ala Ala Gln Val Pro Ala
            100                 105                 110

Arg Tyr Gly Ile Arg Pro Ser Asp Tyr Asp Tyr Trp Gly Glu Gly Thr
        115                 120                 125
```

Leu Val Thr Val Ser Ser
    130

<210> SEQ ID NO 43
<211> LENGTH: 134
<212> TYPE: PRT
<213> ORGANISM: Artificial Sequence
<220> FEATURE:
<223> OTHER INFORMATION: Camelid

<400> SEQUENCE: 43

Glu Val Gln Leu Val Glu Ser Gly Gly Asp Ser Val Gln Ala Gly Gly
1               5                   10                  15

Ser Leu Gln Leu Ser Cys Lys Ala Ser Gly Tyr Thr Tyr Asn Ser Arg
            20                  25                  30

Val Asp Ile Arg Ser Met Gly Trp Phe Arg Gln Tyr Pro Gly Lys Glu
        35                  40                  45

Arg Glu Gly Val Ala Thr Ile Asn Ile Arg Asn Ser Val Thr Tyr Tyr
    50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Ala Leu Lys Pro Glu Asp Thr Ala
                85                  90                  95

Met Tyr Tyr Cys Ala Leu Ser Asp Arg Phe Ala Ala Gln Val Pro Thr
            100                 105                 110

Arg Tyr Gly Ile Arg Pro Ser Asp Tyr Asn Tyr Trp Gly Gln Gly Thr
        115                 120                 125

Gln Val Thr Val Ser Ser
    130

<210> SEQ ID NO 44
<211> LENGTH: 663
<212> TYPE: PRT
<213> ORGANISM: Homo sapiens

<400> SEQUENCE: 44

Met Gly Arg Tyr Arg Ile Arg Val Ala Thr Gly Ala Trp Leu Phe Ser
1               5                   10                  15

Gly Ser Tyr Asn Arg Val Gln Leu Trp Leu Val Gly Thr Arg Gly Glu
            20                  25                  30

Ala Glu Leu Glu Leu Gln Leu Arg Pro Ala Arg Gly Glu Glu Glu Glu
        35                  40                  45

Phe Asp His Asp Val Ala Glu Asp Leu Gly Leu Leu Gln Phe Val Arg
    50                  55                  60

Leu Arg Lys His His Trp Leu Asp Asp Ala Trp Phe Cys Asp Arg
65                  70                  75                  80

Ile Thr Val Gln Gly Pro Gly Ala Cys Ala Glu Val Ala Phe Pro Cys
                85                  90                  95

Tyr Arg Trp Val Gln Gly Glu Asp Ile Leu Ser Leu Pro Glu Gly Thr
            100                 105                 110

Ala Arg Leu Pro Gly Asp Asn Ala Leu Asp Met Phe Gln Lys His Arg
        115                 120                 125

Glu Lys Glu Leu Lys Asp Arg Gln Gln Ile Tyr Cys Trp Ala Thr Trp
    130                 135                 140

Lys Glu Gly Leu Pro Leu Thr Ile Ala Ala Asp Arg Lys Asp Asp Leu
145                 150                 155                 160

-continued

```
Pro Pro Asn Met Arg Phe His Glu Glu Lys Arg Leu Asp Phe Glu Trp
            165                 170                 175
Thr Leu Lys Ala Gly Ala Leu Glu Met Ala Leu Lys Arg Val Tyr Thr
        180                 185                 190
Leu Leu Ser Ser Trp Asn Cys Leu Glu Asp Phe Asp Gln Ile Phe Trp
    195                 200                 205
Gly Gln Lys Ser Ala Leu Ala Glu Lys Val Arg Gln Cys Trp Gln Asp
210                 215                 220
Asp Glu Leu Phe Ser Tyr Gln Phe Leu Asn Gly Ala Asn Pro Met Leu
225                 230                 235                 240
Leu Arg Arg Ser Thr Ser Leu Pro Ser Arg Leu Val Leu Pro Ser Gly
                245                 250                 255
Met Glu Glu Leu Gln Ala Gln Leu Glu Lys Glu Leu Gln Asn Gly Ser
            260                 265                 270
Leu Phe Glu Ala Asp Phe Ile Leu Leu Asp Gly Ile Pro Ala Asn Val
        275                 280                 285
Ile Arg Gly Glu Lys Gln Tyr Leu Ala Ala Pro Leu Val Met Leu Lys
    290                 295                 300
Met Glu Pro Asn Gly Lys Leu Gln Pro Met Val Ile Gln Ile Gln Pro
305                 310                 315                 320
Pro Asn Pro Ser Ser Pro Thr Pro Thr Leu Phe Leu Pro Ser Asp Pro
                325                 330                 335
Pro Leu Ala Trp Leu Leu Ala Lys Ser Trp Val Arg Asn Ser Asp Phe
            340                 345                 350
Gln Leu His Glu Ile Gln Tyr His Leu Leu Asn Thr His Leu Val Ala
        355                 360                 365
Glu Val Ile Ala Val Ala Thr Met Arg Cys Leu Pro Gly Leu His Pro
    370                 375                 380
Ile Phe Lys Phe Leu Ile Pro His Ile Arg Tyr Thr Met Glu Ile Asn
385                 390                 395                 400
Thr Arg Ala Arg Thr Gln Leu Ile Ser Asp Gly Gly Ile Phe Asp Lys
                405                 410                 415
Ala Val Ser Thr Gly Gly Gly His Val Gln Leu Leu Arg Arg Ala
            420                 425                 430
Ala Ala Gln Leu Thr Tyr Cys Ser Leu Cys Pro Pro Asp Asp Leu Ala
        435                 440                 445
Asp Arg Gly Leu Leu Gly Leu Pro Gly Ala Leu Tyr Ala His Asp Ala
    450                 455                 460
Leu Arg Leu Trp Glu Ile Ile Ala Arg Tyr Val Glu Gly Ile Val His
465                 470                 475                 480
Leu Phe Tyr Gln Arg Asp Asp Ile Val Lys Gly Asp Pro Glu Leu Gln
                485                 490                 495
Ala Trp Cys Arg Glu Ile Thr Glu Val Gly Leu Cys Gln Ala Gln Asp
            500                 505                 510
Arg Gly Phe Pro Val Ser Phe Gln Ser Gln Ser Gln Leu Cys His Phe
        515                 520                 525
Leu Thr Met Cys Val Phe Thr Cys Thr Ala Gln His Ala Ala Ile Asn
    530                 535                 540
Gln Gly Gln Leu Asp Trp Tyr Ala Trp Val Pro Asn Ala Pro Cys Thr
545                 550                 555                 560
Met Arg Met Pro Pro Thr Thr Lys Glu Asp Val Thr Met Ala Thr
                565                 570                 575
Val Met Gly Ser Leu Pro Asp Val Arg Gln Ala Cys Leu Gln Met Ala
```

```
                      580                 585                 590
Ile Ser Trp His Leu Ser Arg Arg Gln Pro Asp Met Val Pro Leu Gly
                    595                 600                 605

His His Lys Glu Lys Tyr Phe Ser Gly Pro Lys Pro Lys Ala Val Leu
            610                 615                 620

Asn Gln Phe Arg Thr Asp Leu Glu Lys Leu Glu Lys Glu Ile Thr Ala
625                 630                 635                 640

Arg Asn Glu Gln Leu Asp Trp Pro Tyr Glu Tyr Leu Lys Pro Ser Cys
                645                 650                 655

Ile Glu Asn Ser Val Thr Ile
            660

<210> SEQ ID NO 45
<211> LENGTH: 366
<212> TYPE: DNA
<213> ORGANISM: Artificial Sequence
<220> FEATURE:
<223> OTHER INFORMATION: Camelid

<400> SEQUENCE: 45
gaggtgcagc tggtggagtc tgggggaggt tcggtgcagg ctggagggtc tctgaggatc      60
tcctgtacag cctctggatt cacttttgat gacactgaca tgggctggta ccgccagact     120
ctaggaaatg ggtgcgagtt ggtttctcag attagtaatg atggtagtac attctataga     180
gattccgtga agggccgatt caccatctcc tgggaccgcg tcaacaacac ggtgtatctg     240
caaatgagcg ccctgagacc tgaggacacg gccatgtatt actgcaatat caacgggtgt     300
aggagaccct cgtacaatct tcacttgaac gcatggggcc aggggacaca ggtcaccgtc     360
tcctca                                                               366

<210> SEQ ID NO 46
<211> LENGTH: 372
<212> TYPE: DNA
<213> ORGANISM: Artificial Sequence
<220> FEATURE:
<223> OTHER INFORMATION: Camelid

<400> SEQUENCE: 46
caggtgcagc tggtggagtc tgggggaggc tcggtgcagg ctggagggtc tctgacactg      60
tcctgtgtag cctctggata cggctacagt gccacgtgca tgggctggtt ccgccaggct     120
ccagggaagg agcgcgaggg ggtcgcgtct atttcacctt atggtgttag aaccttctat     180
gccgactccg cgaaaggccg attcaccgtc tcccgagaca acgccaagaa cacgctgtat     240
ctgcaaatga acagcctgaa acctgaggac acgtccgtgt actactgtgc ggccggttcg     300
ggcgttggtg tttgttcact ttcgtatcca tacacctact ggggccaggg gacccaggtc     360
accgtctcct ca                                                        372

<210> SEQ ID NO 47
<211> LENGTH: 372
<212> TYPE: DNA
<213> ORGANISM: Artificial Sequence
<220> FEATURE:
<223> OTHER INFORMATION: Camelid

<400> SEQUENCE: 47
caggtgcagc tggtggagtc tgggggaggc tcggtgcggg ctggagagtc tctgagactc      60
tcctgtgtag cctctagatc catctatgtt tggtactgca tgggctggtt ccgccaggct     120
```

```
gcagggaagg agcgcgaggg ggtcggaagt atgttcgttg gtggcggtag gacatattat    180
gacgactccg tcaagggccg attcaccatc tcccaagaca aggccaagaa cacgctgtat    240
ctgcaaatgg acaacctggc acctgaagac actgccatgt attactgtgc ggctgggcgc    300
tgcggtggca actggctgag aagcaatgct ttcgacaaat ggggccaggg gacactggtc    360
accgtctcct ca                                                        372
```

<210> SEQ ID NO 48
<211> LENGTH: 369
<212> TYPE: DNA
<213> ORGANISM: Artificial Sequence
<220> FEATURE:
<223> OTHER INFORMATION: Camelid

<400> SEQUENCE: 48

```
gatgtgcagc tggtggagtc tgggggaggc tcggtgcagg ctggagggtc tctgagactc     60
tcctgtgcag ccactggaaa cacctacatt agccgctgca tgggctggtt ccgccagcct    120
ccagggaagg agcgcgaggt ggtcgcacgt atttataccg actctggtaa tacatactat    180
cccgacgccg tggagggccg attcaccatc tcccaagaca acgccaagaa cacgatatat    240
ctgcaaatga acagcctgaa acctgacgac accgccgtgt actactgtgt gctctcagag    300
gccgtctgta caaagaacc tggggacttt cgttactggg ccaggggac ccaggtcact    360 gtctcctca                                                             369
```

<210> SEQ ID NO 49
<211> LENGTH: 122
<212> TYPE: PRT
<213> ORGANISM: Artificial Sequence
<220> FEATURE:
<223> OTHER INFORMATION: Camelid

<400> SEQUENCE: 49

```
Glu Val Gln Leu Val Glu Ser Gly Gly Gly Ser Val Gln Ala Gly Gly
1               5                   10                  15

Ser Leu Arg Ile Ser Cys Thr Ala Ser Gly Phe Thr Phe Asp Asp Thr
            20                  25                  30

Asp Met Gly Trp Tyr Arg Gln Thr Leu Gly Asn Gly Cys Glu Leu Val
        35                  40                  45

Ser Gln Ile Ser Asn Asp Gly Ser Thr Phe Tyr Arg Asp Ser Val Lys
    50                  55                  60

Gly Arg Phe Thr Ile Ser Trp Asp Arg Val Asn Asn Thr Val Tyr Leu
65                  70                  75                  80

Gln Met Ser Ala Leu Arg Pro Glu Asp Thr Ala Met Tyr Tyr Cys Asn
                85                  90                  95

Ile Asn Gly Cys Arg Arg Pro Ser Tyr Asn Leu His Leu Asn Ala Trp
            100                 105                 110

Gly Gln Gly Thr Gln Val Thr Val Ser Ser
        115                 120
```

<210> SEQ ID NO 50
<211> LENGTH: 124
<212> TYPE: PRT
<213> ORGANISM: Artificial Sequence
<220> FEATURE:
<223> OTHER INFORMATION: Camelid

<400> SEQUENCE: 50

Gln Val Gln Leu Val Glu Ser Gly Gly Gly Ser Val Gln Ala Gly Gly

```
                1               5                      10                     15
Ser Leu Thr Leu Ser Cys Val Ala Ser Gly Tyr Gly Tyr Ser Ala Thr
                20                      25                     30

Cys Met Gly Trp Phe Arg Gln Ala Pro Gly Lys Glu Arg Glu Gly Val
            35                      40                  45

Ala Ser Ile Ser Pro Tyr Gly Val Arg Thr Phe Tyr Ala Asp Ser Ala
        50                      55                  60

Lys Gly Arg Phe Thr Val Ser Arg Asp Asn Ala Lys Asn Thr Leu Tyr
 65                      70                  75                  80

Leu Gln Met Asn Ser Leu Lys Pro Glu Asp Thr Ser Val Tyr Tyr Cys
                85                      90                  95

Ala Ala Gly Ser Gly Val Gly Val Cys Ser Leu Ser Tyr Pro Tyr Thr
            100                     105                 110

Tyr Trp Gly Gln Gly Thr Gln Val Thr Val Ser Ser
            115                     120
```

<210> SEQ ID NO 51
<211> LENGTH: 124
<212> TYPE: PRT
<213> ORGANISM: Artificial Sequence
<220> FEATURE:
<223> OTHER INFORMATION: Camelid

<400> SEQUENCE: 51

```
Gln Val Gln Leu Val Glu Ser Gly Gly Gly Ser Val Arg Ala Gly Glu
 1               5                      10                     15

Ser Leu Arg Leu Ser Cys Val Ala Ser Arg Ser Ile Tyr Val Trp Tyr
                20                      25                     30

Cys Met Gly Trp Phe Arg Gln Ala Ala Gly Lys Glu Arg Glu Gly Val
            35                      40                  45

Gly Ser Met Phe Val Gly Gly Arg Thr Tyr Tyr Asp Asp Ser Val
        50                      55                  60

Lys Gly Arg Phe Thr Ile Ser Gln Asp Lys Ala Lys Asn Thr Leu Tyr
 65                      70                  75                  80

Leu Gln Met Asp Asn Leu Ala Pro Glu Asp Thr Ala Met Tyr Tyr Cys
                85                      90                  95

Ala Ala Gly Arg Cys Gly Gly Asn Trp Leu Arg Ser Asn Ala Phe Asp
            100                     105                 110

Lys Trp Gly Gln Gly Thr Leu Val Thr Val Ser Ser
            115                     120
```

<210> SEQ ID NO 52
<211> LENGTH: 123
<212> TYPE: PRT
<213> ORGANISM: Artificial Sequence
<220> FEATURE:
<223> OTHER INFORMATION: Camelid

<400> SEQUENCE: 52

```
Asp Val Gln Leu Val Glu Ser Gly Gly Gly Ser Val Gln Ala Gly Gly
 1               5                      10                     15

Ser Leu Arg Leu Ser Cys Ala Ala Thr Gly Asn Thr Tyr Ile Ser Arg
                20                      25                     30

Cys Met Gly Trp Phe Arg Gln Pro Pro Gly Lys Glu Arg Glu Val Val
            35                      40                  45

Ala Arg Ile Tyr Thr Asp Ser Gly Asn Thr Tyr Tyr Pro Asp Ala Val
        50                      55                  60
```

Glu Gly Arg Phe Thr Ile Ser Gln Asp Asn Ala Lys Asn Thr Ile Tyr
65                  70                  75                  80

Leu Gln Met Asn Ser Leu Lys Pro Asp Asp Thr Ala Val Tyr Tyr Cys
                85                  90                  95

Val Leu Ser Glu Ala Val Cys Thr Lys Glu Pro Gly Asp Phe Arg Tyr
            100                 105                 110

Trp Gly Gln Gly Thr Gln Val Thr Val Ser Ser
            115                 120

<210> SEQ ID NO 53
<211> LENGTH: 190
<212> TYPE: PRT
<213> ORGANISM: Ebola virus

<400> SEQUENCE: 53

Ala Lys Ala Thr Gly Arg Tyr Asn Leu Ile Ser Pro Lys Lys Asp Leu
1               5                   10                  15

Glu Lys Gly Val Val Leu Ser Asp Leu Cys Asn Phe Leu Val Ser Gln
            20                  25                  30

Thr Ile Gln Gly Trp Lys Val Tyr Trp Ala Gly Ile Glu Phe Asp Val
        35                  40                  45

Thr His Lys Gly Met Ala Leu Leu His Arg Leu Lys Thr Asn Asp Phe
    50                  55                  60

Ala Pro Ala Trp Ser Met Thr Arg Asn Leu Phe Pro His Leu Phe Gln
65                  70                  75                  80

Asn Pro Asn Ser Thr Ile Glu Ser Pro Leu Trp Ala Leu Arg Val Ile
                85                  90                  95

Leu Ala Ala Gly Ile Gln Asp Gln Leu Ile Asp Gln Ser Leu Ile Glu
            100                 105                 110

Pro Leu Ala Gly Ala Leu Gly Leu Ile Ser Asp Trp Leu Leu Thr Thr
        115                 120                 125

Asn Thr Asn His Phe Asn Met Arg Thr Gln Arg Val Lys Glu Gln Leu
    130                 135                 140

Ser Leu Lys Met Leu Ser Leu Ile Arg Ser Asn Ile Leu Lys Phe Ile
145                 150                 155                 160

Asn Lys Leu Asp Ala Leu His Val Val Asn Tyr Asn Gly Leu Leu Ser
                165                 170                 175

Ser Ile Glu Ile Ile Leu Glu Phe Asn Ser Ser Leu Ala Ile
            180                 185                 190

<210> SEQ ID NO 54
<211> LENGTH: 486
<212> TYPE: DNA
<213> ORGANISM: Artificial Sequence
<220> FEATURE:
<223> OTHER INFORMATION: Camelid

<400> SEQUENCE: 54
atgggtgatg tgcagctggt ggagtctggg ggagactcgg tgcgggctgg agggtctctt      60
caaatgggtg atgtgcagct ggtggagtct gggggagact cggtgcgggc tggagggtct     120
cttcaactct cctgtaaagc ctctggatac acctacaata gtagtcga tatcagatct       180 atgggctggt tccgccagta tccaggaaag gagcgcgagg gggtcgctac tattaatatt     240
cgtaatagtg tcacatacta tgccgactcc gtgaagggcc gattcaccat ctcccaagac     300
aacgccaaga cacggtgta tctgcaaatg aacgccctga acctgaggga cactgccatg     360
tactactgtg cgttgtcaga cagattcgcg gcgcaggtac ctgccaggta cggaatacgg     420

```
cctctgact ataactactg gggtgagggg accctggtca ccgtctcctc aagctctggt    480
ctcgag                                                              486
```

<210> SEQ ID NO 55
<211> LENGTH: 141
<212> TYPE: PRT
<213> ORGANISM: Artificial Sequence
<220> FEATURE:
<223> OTHER INFORMATION: Camelid

<400> SEQUENCE: 55

```
Met Gly Asp Val Gln Leu Val Glu Ser Gly Gly Asp Ser Val Arg Ala
1               5                   10                  15

Gly Gly Ser Leu Gln Leu Ser Cys Lys Ala Ser Gly Tyr Thr Tyr Asn
            20                  25                  30

Ser Arg Val Asp Ile Arg Ser Met Gly Trp Phe Arg Gln Tyr Pro Gly
        35                  40                  45

Lys Glu Arg Glu Gly Val Ala Thr Ile Asn Ile Arg Asn Ser Val Thr
    50                  55                  60

Tyr Tyr Ala Asp Ser Val Lys Gly Arg Phe Thr Ile Ser Gln Asp Asn
65                  70                  75                  80

Ala Lys Asn Thr Val Tyr Leu Gln Met Asn Ala Leu Lys Pro Glu Asp
                85                  90                  95

Thr Ala Met Tyr Tyr Cys Ala Leu Ser Asp Arg Phe Ala Ala Gln Val
            100                 105                 110

Pro Ala Arg Tyr Gly Ile Arg Pro Ser Asp Tyr Asn Tyr Trp Gly Glu
        115                 120                 125

Gly Thr Leu Val Thr Val Ser Ser Ser Gly Leu Glu
    130                 135                 140
```

<210> SEQ ID NO 56
<211> LENGTH: 126
<212> TYPE: PRT
<213> ORGANISM: Artificial Sequence
<220> FEATURE:
<223> OTHER INFORMATION: Camelid

<400> SEQUENCE: 56

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Trp Leu Asp Arg Thr Ala Gly Gly
            100                 105                 110

His Thr Tyr Trp Gly Gln Gly Thr Leu Val Thr Val Ser Ser
        115                 120                 125
```

SINGLE DOMAIN ANTIBODIES DIRECTED AGAINST HUMAN IMMUNODEFICIENCY VIRUS

CROSS REFERENCE TO RELATED APPLICATIONS

This application claims the benefit of U.S. Provisional Patent Application No. 62/249,868 filed on Nov. 2, 2015, the contents of which are incorporated herein by reference in their entirety.

SEQUENCE LISTING

The present application is being filed along with a Sequence Listing in ASCII text format in lieu of a paper copy. The Sequence Listing is provided as a file titled "sequence listing.txt," created Oct. 27, 2016, and is 58 kilobytes in size. The information in the electronic format of the Sequence Listing is incorporated herein by reference in its entirety.

BACKGROUND

The use of single-domain antibodies (sdAbs) as single antigen-binding proteins or as an antigen-binding domain in larger protein or polypeptide offers a number of significant advantages over the use of conventional antibodies or antibody fragments. The advantages of sdAbs include: only a single domain is required to bind an antigen with high affinity and with high selectivity; sdAbs can be expressed from a single gene and require no post-translational modification; sdAbs are highly stable to denaturing agents or conditions including heat, pH, and proteases; sdAbs are inexpensive to prepare; and sdAbs can access targets and epitopes not accessible to conventional antibodies.

There are a number of diseases or conditions, such as viral infections or cancer, that are caused by aberrant intracellular or transmembrane components such as nucleotides and proteins. Elimination of the aberrant components can be used to prevent or treat the diseases or conditions. There are a number of pharmacological compounds available for treatment of such diseases, but the compounds can be ineffective, undeliverable, or toxic to unaffected cells.

Other treatments include the use of therapeutic proteins or agents that contain an exogenous targeting sequence so that the therapeutic agent can be recognized by receptors in the cell membrane, enabling the therapeutic agent to cross the cell membrane and enter the cell. Once the therapeutic agent is inside the cell, the therapeutic agent can interact with the target component in order to treat the disease. However, the use of exogenous targeting sequences can limit the cell type that is targeted by the therapeutic agent, and adds to the cost of manufacturing the therapeutic agent.

For the foregoing reasons, there is a need for compositions and methods to treat or prevent a disease that do not rely on exogenous targeting sequences or chemical compositions in order to enter the cell, and that are effective in targeting only the affected cells in the body.

The present invention relates to single-domain antibodies (sdAbs), proteins and polypeptides comprising the sdAbs. The sdAbs are directed against targets that cause a condition or disease. The invention also includes nucleic acids encoding the sdAbs, proteins and polypeptides, and compositions comprising the sdAbs. The invention includes the use of the compositions, sdAbs, proteins or polypeptides for prophylactic, therapeutic or diagnostic purposes. The invention also includes the use of monoclonal antibodies directed towards the sdAbs of the invention.

SUMMARY

The present invention is directed to sdAbs used to treat or prevent a condition or disease. One embodiment is directed to an anti-Human Immunodeficiency Virus Type 1 (HIV-1) reverse transcriptase single domain antibody (sdAb). In one aspect, the anti-HIV-1 reverse transcriptase sdAb comprises the amino acid sequence as set forth in SEQ ID NO:27. The invention also includes a method of treating a disease, preventing development of a disease, or preventing recurrence of a disease in a subject using an anti-HIV-1 reverse transcriptase sdAb by administration of effective amount of the anti-HIV-1 reverse transcriptase sdAb to a subject in need thereof. The subject can be a mammal, such as a human. The anti-HIV-1 reverse transcriptase sdAb can be administered in combination with one or more compounds such as, for example, a protease inhibitor. Administration of an effective amount of the anti-HIV-1 reverse transcriptase sdAb to a subject in need thereof can be by intravenous administration, intramuscular administration, oral administration, rectal administration, enteral administration, parenteral administration, intraocular administration, subcutaneous administration, transdermal administration, administered as eye drops, administered as nasal spray, administered by inhalation or nebulization, topical administration, and administered as an implantable drug.

In another embodiment, the invention is directed to an isolated polypeptide having the amino acid sequence as set forth in SEQ ID NO:27. In another embodiment, the invention includes an antibody directed toward the polypeptide of SEQ ID NO:27.

It is also contemplated that the invention includes a method of measuring the levels of an anti-HIV-1 reverse transcriptase sdAb in a sample from a subject, the method comprising the steps of: a) generating a mouse monoclonal antibody directed against one or more domains of a polypeptide comprising the amino acid sequence as set forth in SEQ ID NO:27; b) obtaining a sample from the subject; c) performing a quantitative immunoassay with the mouse monoclonal antibody and the sample to determine the amount of sdAb in a subject; thus measuring the amount of sdAb in the subject. In one aspect, the quantitative immunoassay comprises an enzyme-linked immunosorbent assay (ELISA), specific analyte labeling and recapture assay (SALRA), liquid chromatography, mass spectrometry, fluorescence-activated cell sorting, or a combination thereof.

Another embodiment of the invention is directed to an anti-Ebola VP24 sdAb. In one aspect, the anti-Ebola VP24 sdAb comprises the amino acid sequence as set forth in SEQ ID NO:55. The invention also includes a method of treating a disease, preventing development of a disease, or preventing recurrence of a disease in a subject using an anti-Ebola VP24 sdAb by administration of effective amount of the anti-Ebola VP24 sdAb to a subject in need thereof. The subject can be a mammal, such as a human. The anti-Ebola VP24 sdAb can be administered in combination with one or more compounds such as, for example, a protease inhibitor. Administration of an effective amount of the anti-Ebola VP24 sdAb to a subject in need thereof can be by intravenous administration, intramuscular administration, oral administration, rectal administration, enteral administration, parenteral administration, intraocular administration, subcutaneous administration, transdermal administration, administered as eye drops, administered as nasal spray, administered by inhalation or nebulization, topical administration, and administered as an implantable drug.

In another embodiment, the invention is directed to an isolated polypeptide having the amino acid sequence as set forth in SEQ ID NO:55. In another embodiment, the invention includes an antibody directed toward the polypeptide of SEQ ID NO:55.

It is also contemplated that the invention includes a method of measuring the levels of an anti-Ebola VP24 sdAb in a sample from a subject, the method comprising the steps of: a) generating a mouse monoclonal antibody directed against one or more domains of a polypeptide comprising the amino acid sequence as set forth in SEQ ID NO:55; b) obtaining a sample from the subject; c) performing a quantitative immunoassay with the mouse monoclonal antibody and the sample to determine the amount of sdAb in a subject; thus measuring the amount of sdAb in the subject. In one aspect, the quantitative immunoassay comprises an ELISA, SALRA, liquid chromatography, mass spectrometry, fluorescence-activated cell sorting, or a combination thereof.

Yet another embodiment of the invention is directed to an anti-arachidonate 12-lipoxygenase (ALOX12) sdAb. In one aspect, the anti-ALOX12 sdAb comprises the amino acid sequence as set forth in SEQ ID NO:49, SEQ ID NO:50, SEQ ID NO:51, or SEQ ID NO:52. The invention also includes a method of treating a disease, preventing development of a disease, or preventing recurrence of a disease in a subject using an anti-ALOX12 sdAb by administration of effective amount of the anti-ALOX12 sdAb to a subject in need thereof. The subject can be a mammal, such as a human. The anti-ALOX12 sdAb can be administered in combination with one or more compounds. Administration of an effective amount of the anti-ALOX12 sdAb to a subject in need thereof can be by intravenous administration, intramuscular administration, oral administration, rectal administration, enteral administration, parenteral administration, intraocular administration, subcutaneous administration, transdermal administration, administered as eye drops, administered as nasal spray, administered by inhalation or nebulization, topical administration, and administered as an implantable drug.

In another embodiment, the invention is directed to an isolated polypeptide having the amino acid sequence as set forth in SEQ ID NO:49, SEQ ID NO:50, SEQ ID NO:51, or SEQ ID NO:52. In another embodiment, the invention includes an antibody directed toward the polypeptide of SEQ ID NO:49, SEQ ID NO:50, SEQ ID NO:51, or SEQ ID NO:52.

It is also contemplated that the invention includes a method of measuring the levels of an anti-HIV-1 reverse transcriptase sdAb in a sample from a subject, the method comprising the steps of: a) generating a mouse monoclonal antibody directed against one or more domains of a polypeptide comprising the amino acid sequence as set forth in SEQ ID NO:27; b) obtaining a sample from the subject; c) performing a quantitative immunoassay with the mouse monoclonal antibody and the sample to determine the amount of sdAb in a subject; thus measuring the amount of sdAb in the subject. In one aspect, the quantitative immunoassay comprises an ELISA, SALRA, liquid chromatography, mass spectrometry, fluorescence-activated cell sorting, or a combination thereof.

DRAWINGS

These and other features, aspects, and advantages of the present invention will become better understood with regard to the following description, appended claims, and accompanying drawings where:

FIGS. 1 and 2 depict the results of an ELISA using HIV1-9 anti-HIV-1 RT sdAb (SEQ ID NO:27);

FIGS. 3 and 4 depict the results of an ELISA using a dilution series of HIV1-9 anti-HIV-1 RT sdAb (SEQ ID NO:27);

FIGS. 5 through 8 depict the results of an ELISA using VP24-5 anti-Ebola VP24 sdAb (SEQ ID NO:55); and FIGS. 9 and 10 depict the results of an ELISA using a dilution series of VP24-5 anti-Ebola VP24 sdAb (SEQ ID NO:55).

DESCRIPTION

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

The term "antigenic determinant" refers to the epitope on the antigen recognized by the antigen-binding molecule (such as an sdAb or polypeptide of the invention) and more in particular by the antigen-binding site of the antigen-binding molecule. The terms "antigenic determinant" and "epitope" may also be used interchangeably. An amino acid sequence that can bind to, that has affinity for and/or that has specificity for a specific antigenic determinant, epitope, antigen or protein is said to be "against" or "directed against" the antigenic determinant, epitope, antigen or protein.

As used herein, the term "comprise" and variations of the term, such as "comprising" and "comprises," are not intended to exclude other additives, components, integers or steps.

It is contemplated that the sdAbs, polypeptides and proteins described herein can contain so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Conservative amino acid substitutions are well known in the art. Conservative substitutions are substitutions in which one amino acid within the following groups (a)-(e) is substituted by another amino acid within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Other conservative substitutions include: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A "domain" as used herein generally refers to a globular region of an antibody chain, and in particular to a globular region of a heavy chain antibody, or to a polypeptide that essentially consists of such a globular region.

The amino acid sequence and structure of an sdAb is typically made up of four framework regions or "FRs," which are referred to as "Framework region 1" or "FR1"; as "Framework region 2" or"FR2"; as "Framework region 3"

or "FR3"; and as "Framework region 4" or "FR4," respectively. The framework regions are interrupted by three complementarity determining regions or "CDRs," which are referred as "Complementarity Determining Region 1" or "CDR1"; as "Complementarity Determining Region 2" or "CDR2"; and as "Complementarity Determining Region 3" or "CDR3," respectively.

As used herein, the term "humanized sdAb" means an sdAb that has had one or more amino acid residues in the amino acid sequence of the naturally occurring VHH sequence replaced by one or more of the amino acid residues that occur at the corresponding position in a VH domain from a conventional 4-chain antibody from a human. This can be performed by methods that are well known in the art. For example, the FRs of the sdAbs can be replaced by human variable FRs.

As used herein, an "isolated" nucleic acid or amino acid has been separated from at least one other component with which it is usually associated, such as its source or medium, another nucleic acid, another protein/polypeptide, another biological component or macromolecule or contaminant, impurity or minor component.

The term "mammal" is defined as an individual belonging to the class Mammalia and includes, without limitation, humans, domestic and farm animals, and zoo, sports, and pet animals, such as cows, horses, sheep, dogs and cats.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, PBS (phosphate-buffered saline), and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined above, use thereof in the composition of the present invention is contemplated.

A "quantitative immunoassay" refers to any means of measuring an amount of antigen present in a sample by using an antibody. Methods for performing quantitative immunoassays include, but are not limited to, enzyme-linked immunosorbent assay (ELISA), specific analyte labeling and recapture assay (SALRA), liquid chromatography, mass spectrometry, fluorescence-activated cell sorting, and the like.

The term "solution" refers to a composition comprising a solvent and a solute, and includes true solutions and suspensions. Examples of solutions include a solid, liquid or gas dissolved in a liquid and particulates or micelles suspended in a liquid.

The term "specificity" refers to the number of different types of antigens or antigenic determinants to which a particular antigen-binding molecule or antigen-binding protein molecule can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to one of skill in the art, affinity can be determined depending on the specific antigen of interest. Avidity is the measure of the strength of binding between an antigen-binding molecule and the antigen. Avidity is related to both the affinity between an antigenic determinant and its antigen binding site on the antigen-binding molecule and the number of pertinent binding sites present on the antigen-binding molecule. Specific binding of an antigen-binding protein to an antigen or antigenic determinant can be determined by any known manner, such as, for example, Scatchard analysis and/or competitive binding assays, such as radioimmunoassays (RIA), enzyme immunoassays (EIA) and sandwich competition assays.

As used herein, the term "recombinant" refers to the use of genetic engineering methods (for example, cloning, and amplification) used to produce the sdAbs of the invention.

A "single domain antibody," "sdAb" or "VHH" can be generally defined as a polypeptide or protein comprising an amino acid sequence that is comprised of four framework regions interrupted by three complementarity determining regions. This is represented as FR1-CDR1-FR2-CDR2-FR3-CDR3-FR4. An sdAb of the invention also includes a polypeptide or protein that comprises the sdAb amino acid sequence. Typically, sdAbs are produced in camelids such as llamas, but can also be synthetically generated using techniques that are well known in the art. As used herein, the variable domains present in naturally occurring heavy chain antibodies will also be referred to as "VHH domains," in order to distinguish them from the heavy chain variable domains that are present in conventional 4-chain antibodies, referred to as "VH domains," and from the light chain variable domains that are present in conventional 4-chain antibodies, referred to as "VL domains." "VHH" and "sdAb" are used interchangeably herein. The numbering of the amino acid residues of an sdAb or polypeptide is according to the general numbering for VH domains given by Kabat et al. ("Sequence of proteins of immunological interest," US Public Health Services, NIH Bethesda, Md., Publication No. 91). According to this numbering, FR1 of an sdAb comprises the amino acid residues at positions 1-30, CDR1 of an sdAb comprises the amino acid residues at positions 31-36, FR2 of an sdAb comprises the amino acids at positions 36-49, CDR2 of an sdAb comprises the amino acid residues at positions 50-65, FR3 of an sdAb comprises the amino acid residues at positions 66-94, CDR3 of an sdAb comprises the amino acid residues at positions 95-102, and FR4 of an sdAb comprises the amino acid residues at positions 103-113.

The term "synthetic" refers to production by in vitro chemical or enzymatic synthesis.

The term "target" as used herein refers to any component, antigen, or moiety that is recognized by the sdAb. The term "intracellular target" refers to any component, antigen, or moiety present inside a cell. A "transmembrane target" is a component, antigen, or moiety that is located within the cell membrane. An "extracellular target" refers to a component, antigen, or moiety that is located outside of the cell.

A "therapeutic composition" as used herein means a substance that is intended to have a therapeutic effect such as pharmaceutical compositions, genetic materials, biologics, and other substances. Genetic materials include substances intended to have a direct or indirect genetic therapeutic effect such as genetic vectors, genetic regulator elements, genetic structural elements, DNA, RNA and the like. Biologics include substances that are living matter or derived from living matter intended to have a therapeutic effect.

As used herein, the phrases "therapeutically effective amount" and "prophylactically effective amount" refer to an amount that provides a therapeutic benefit in the treatment, prevention, or management of a disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The specific amount that is therapeutically effective can be readily determined by an ordinary medical practitioner, and may vary depending on factors known in the art, such as, e.g., the type of disease, the patient's history and age, the stage of disease, and the administration of other therapeutic agents.

The present invention relates to single-domain antibodies (sdAbs) that are directed against viral and intracellular components, as well as to proteins and polypeptides comprising the sdAbs and nucleotides encoding the proteins and polypeptides. The invention can also relate to sdAbs that are directed against intercellular, transcellular and extracellular targets or antigens. The invention also includes nucleic acids encoding the sdAbs, proteins and polypeptides, and compositions comprising the sdAbs. The invention includes the use of the compositions, sdAbs, proteins or polypeptides for prophylactic, therapeutic or diagnostic purposes.

SdAbs have a number of unique structural characteristics and functional properties which make sdAbs highly advantageous for use as functional antigen-binding domains or proteins. SdAbs functionally bind to an antigen in the absence of a light chain variable domain, and can function as a single, relatively small, functional antigen-binding structural unit, domain or protein. This distinguishes sdAbs from the domains of conventional antibodies, which by themselves do not function as an antigen-binding protein or domain, but need to be combined with conventional antibody fragments such as antigen-binding fragments (Fab) or single chain variable fragments (ScFv) in order to bind an antigen.

SdAbs can be obtained using methods that are well known in the art. For example, one method for obtaining sdAbs includes (a) immunizing a Camelid with one or more antigens, (b) isolating peripheral lymphocytes from the immunized Camelid, obtaining the total RNA and synthesizing the corresponding complementary DNAs (cDNAs), (c) constructing a library of cDNA fragments encoding VHH domains, (d) transcribing the VHH domain-encoding cDNAs obtained in step (c) to messenger RNA (mRNA) using PCR, converting the mRNA to ribosome display format, and selecting the VHH domain by ribosome display, and (e) expressing the VHH domain in a suitable vector and, optionally purifying the expressed VHH domain.

Another method of obtaining the sdAbs of the invention is by preparing a nucleic acid encoding an sdAb using techniques for nucleic acid synthesis, followed by expression of the nucleic acid in vivo or in vitro. Additionally, the sdAb, polypeptides and proteins of the invention can be prepared using synthetic or semi-synthetic techniques for preparing proteins, polypeptides or other amino acid sequences.

The sdAbs of the invention will generally bind to all naturally occurring or synthetic analogs, variants, mutants, alleles, parts and fragments of the target, or at least to those analogs, variants, mutants, alleles, parts and fragments of the target that contain one or more antigenic determinants or epitopes that are essentially the same as the antigenic determinant or epitope to which the sdAbs of the invention bind in the wild-type target. The sdAbs of the invention may bind to such analogs, variants, mutants, alleles, parts and fragments with an affinity and/or specificity that is the same as, or that is higher than or lower than the affinity and specificity with which the sdAbs of the invention bind to the wild-type target. It is also contemplated within the scope of the invention that the sdAbs of the invention bind to some analogs, variants, mutants, alleles, parts and fragments of the target but not to others. In addition, the sdAb of the invention may be humanized, and may be monovalent or multivalent, and/or multispecific. Additionally, the sdAbs of the invention can bind to the phosphorylated form of the target protein as well as the unphosphorylated form of the target protein. sdAbs can be linked to other molecules such as albumin or other macromolecules.

In addition, it is within the scope of the invention that the sdAbs are multivalent, that is, the sdAb can have two or more proteins or polypeptides which are directed against two or more different epitopes of the target. In such a multivalent sdAb, the protein or polypeptide may be directed, for example, against the same epitopes, substantially equivalent epitopes, or different epitopes. The different epitopes may be located on the same target, or it could be on two or more different targets.

It is also contemplated that the sequence of one or more sdAbs of the invention may be connected or joined with one or more linker sequences. The linker can be, for example, a protein sequence containing a combination of serines, glycines and alanines.

It is also within the scope of the invention to use parts, fragments, analogs, mutants, variants, alleles and/or derivatives of the sdAbs of the invention, as long as these are suitable for the described uses.

Since the sdAbs of the invention are mainly intended for therapeutic and/or diagnostic use, they are directed against mammalian, preferably human, targets. However, it is possible that the sdAbs described herein are cross-reactive with targets from other species, for example, with targets from one or more other species of primates or other animals (for example, mouse, rat, rabbit, pig or dog), and in particular in animal models for diseases and disorders associated with the disease associated with the targets.

In another aspect, the invention relates to a nucleic acid that encodes an sdAb of the invention. Such a nucleic acid may be, for example, in the form of a genetic construct.

In another aspect, the invention relates to host or host cell that expresses or is capable of expressing an sdAb of the invention, and/or that contains a nucleic acid encoding an sdAb of the invention. Sequences of the sdAbs can be used to insert into the genome of any organism to create a genetically modified organism (GMO). Examples include, but are not limited to, plants, bacteria, viruses, and animals.

The invention further relates to methods for preparing or generating the sdAbs, nucleic acids encoding the sdAbs, host cells expressing or capable of expressing such sdAbs, products and compositions containing the sdAbs of the invention.

The invention further relates to applications and uses of the sdAbs, the nucleic acids encoding the sdAbs, host cells, products and compositions described herein. Such a product or composition may, for example, be a pharmaceutical composition for treatment or prevention of a disease, or a product or composition for diagnostic use. The sdAbs can be used in a variety of assays, for example ELISA assays and mass spectrometry assays to measure the serum and tissue levels of the sdAbs.

In another aspect, a nucleic acid encoding one or more sdAbs of the invention can be inserted into the genome of an organism to treat or prevent diseases.

The present invention generally relates to sdAbs, as well as to proteins or polypeptides comprising or essentially consisting of one or more of such sdAbs, that can be used for prophylactic, therapeutic and/or diagnostic purposes.

The methods and compositions detailed in the present invention can be used to treat diseases described herein, and can be used with any dosage and/or formulation described herein or otherwise known, as well as with any route of administration described herein or otherwise known to one of skill in the art.

The sdAbs of the invention can be used for treatment and prevention of diseases caused by viruses or by aberrant cellular proteins. The sdAbs of the present invention can also be used for treatment and prevention of diseases. The sdAbs of the invention can be used to target diseases when there is an overexpression of an intracellular molecule. They can also be used to treat viral infections by targeting intracellular viral proteins in infected cells. Blocking production of viral proteins, such as, for example, HIV-1 reverse transcriptase, can block the viral life-cycle.

The sdAbs of the invention can also target intracellular viral proteins such as Ebola VP24 and thus block Ebola's ability to shut down the host's anti-viral immune response.

The sdAbs of the invention can be used with one or more compounds. For example, the sdAb of the invention can be used with JAK/STAT inhibitors such as, for example, Curcumin, Resveratrol, Cucurbitacin A, B, E, I, Q, Flavopiridol, Deoxytetrangomycin, Cyclopentenone derivatives, N-Acylhomoserine Lactone, Indirubin derivatives, Meisoindigo, Tyrphostins, Platinum-containing compounds (e.g., IS3-295), Peptidomimetics, antisense oligonucleotides, S3I-201, phosphotyrosin tripeptide derivatives, HIV protease inhibitors (e.g., nelfinavir, indinavir, saquinavir, & ritornavir), JSI-124, XpYL, Ac-pYLPQTV-NH2, ISS 610, CJ-1383, pyrimethamine, Metformin, Atiprimod, S3I-M2001, STX-0119; N-[2-(1,3,4-oxadiazolyl)]-4 quinolinecarboxamide derivative, S3I-1757, LY5; 5,8-dioxo-6(pyridin-3-ylamino)-5,8,-dihydro-naphthalene-1-sulfonamide, withacinstin, Stattic, STA-21, LLL-3, LLL12, XZH-5, SF-1066, SF-1087, 17o, Cryptotanshinone, FLL32, FLL62, C188-9, BP-1108 and BP-1075, Galiellalactone, JQ1, 5, 15 DPP, WP1066, Niclosamide, SD1008, Nifuroxazide, Cryptotanshinone, BBI quinone, and Ruxolitnib Phosphate. The one or more compounds can increase the therapeutic response and augment the effectiveness of the sdAbs of the invention. In addition, the effectiveness of the sdAbs can be increased by combining it with peptides, peptidomimetics, and other drugs, such as, for example, but not limited to, cimetidine, atorvastatin, celecoxib, metformin, and cimetidine.

It is also contemplated that one or more sdAbs of the invention can be combined, or the sdAbs of the invention can be combined with other sdAbs.

It is contemplated that certain sdAbs of the invention can cross the cell membrane and enter the cell without the aid of additional targeting protein sequences on the sdAb, and without the aid of exogenous compounds that direct the sdAb to bind to the cell surface receptors and cross the cell membrane.

After crossing the cell membrane, these sdAbs can target transmembrane or intracellular molecules or antigens. These targets can be, for example, proteins, carbohydrates, lipids, nucleic acids, mutated proteins, viral proteins, and prions. The sdAb targets may function as enzymes, structural proteins of the cell, intracellular portions of cell membrane molecules, molecules within the membranes of organelles, any type of RNA molecule, any regions of DNA or chromosome, methylated or unmethylated nucleic acids, partially assembled molecules within the synthesis mechanism of the cell, second messenger molecules, and molecules within cell signaling mechanisms. Targets may include all molecules in the cytoplasm, nucleus, organelles, and cell membrane. Molecules destined for secretion or placement in the cell membrane can be targeted within the cytoplasm before leaving the cell.

The sdAb targets can be in humans, animals, plants, fungi, parasites, protists, bacteria, viruses, prions, prokaryotic cells, and eukaryotic cells. Some examples of intercellular and intracellular signaling molecules and protein groups that can be targeted by the sdAbs of the invention are: oncogene products, hormones, cytokines, growth factors, neurotransmitters, kinases (including tyrosine kinase, serine kinase, and threonine kinase), phosphatases, ubiquitin, cyclic nucleotides, cyclases (adenylyl and guanylyl), G proteins, phosphodiesterases, GTPase superfamily, immunoglobulins (antibodies, Fab fragments, binders, sdAbs), immunoglobulin superfamily, inositol phosphate lipids, steroid receptors, calmodulin, CD group (e.g., CD4, CD8, CD28, etc.), transcription factors, TGF-beta, TNF-alpha and beta, TNF ligand superfamily, notch receptor signaling molecules, hedgehog receptor signaling molecules, Wnt receptor signaling molecules, toll-like receptor signaling molecules, caspases, actin, myosin, myostatin, 12-lipoxygenase, 15-lipoxygenase, lipoxygenase superfamily, reverse transcriptase, viruses and their proteins, amyloid proteins, collagen, G protein coupled receptors, mutated normal proteins, prions, Ras, Raf, Myc, Src, BCR/ABL, MEK, Erk, Mos, Tp12, MLK3, TAK, DLK, MKK, p38, MAPK, MEKK, ASK, SAPK, JNK, BMK, MAP, JAK, PI3K, cyclooxygenase, STAT1, STAT2, STAT3, STAT4, STAT5a, STAT5b, STAT6, Myc, p53, BRAF, NRAS, KRAS, HRAS and chemokines.

HIV is a retrovirus that causes acquired immunodeficiency syndrome (AIDS) in humans. AIDS results in progressive failure of the infected individual's immune system, which results in the development of life-threatening opportunistic infections and cancers. The average survival time after infection with HIV is estimated to be 9 to 11 years without treatment HIV is transmitted as single-stranded, positive-sense, enveloped RNA virus. Upon entry into the target cell, the viral RNA genome is reverse transcribed into double-stranded DNA by a virally encoded reverse transcriptase (RT) that is transported along with the viral genome in the virus particle. RT is an RNA-dependent DNA polymerase and also has RNaseH activity. The resulting viral DNA is then imported into the host cell nucleus and integrated into the cellular DNA by a virally encoded integrase and host co-factors. Once integrated, the virus may become latent for months or years. Alternatively, the virus may be transcribed, producing new RNA genomes and viral proteins that are packaged and released from the cell as new virus particles.

Two types of HIV have been characterized: HIV-1 and HIV-2. HIV-1 is more virulent, more infective, and is the cause of the majority of HIV infections globally. HIV-2 is largely confined to West Africa.

Anti-HIV RT sdAbs were developed to target HIV-1 reverse transcriptase. The anti-HIV-1 RT sdAb may successfully treat individuals infected with HIV either alone or in combination with other retroviral agents. Using methods that are well-known in the art, recombinant HIV-1 reverse transcriptase protein (Creative Biomart, Shirley, N.Y.) (SEQ ID NO:1) was used to generate sdAbs that are directed against or can bind to an epitope of HIV-1 RT.

The protein sequence used for immunization of a camel of the recombinant HIV-1 reverse transcriptase protein (SEQ ID NO:1) was PISPIETVPVKLKPGMDGPKVKQWPLT EEKIKALVEICAELEEEGKISRIGPENPYNTPVFAIKK-KDSTKWRKLVDFRELNKRTQDF WEVQLGIPH-PAGLKKKKSVTVLDVGDAYFSIPLDEDFRKYTAFTIP-STNNETPGTRYQY NVLPQGWKGSPAIFQSSMTKILEPFRKQNPDIVIY-QYVDDLYVGSDLEIGQHRTKVEELR QHLWRWGFYT-PDKKHQKEPPFLWMGYELHPDKWTVQPIVLPEKD-SWTVNDIQK As a result of the immunization, several sdAbs were obtained and screened. The DNA sequences of the anti-HIV-1 RT sdAbs are listed below:

```
HIV1-1 (SEQ ID NO: 2):
5'-gatgtgcagctggtggagtctgggggaggctcggtgcaggctggagg gtctctgagactctcctgtgcagcctctgtttacagctacaacacaaact gcatgggttggttccgccaggctccagggaaggagcgcgagggggtcgca gttatttatgctgctggtggattaacatactatgccgactccgtgaaggg ccgattcaccatctcccaggagaatggcaagaatacggtgtacctgacga tgaaccgcctgaaacctgaggacactgccatgtactactgtgcggcaaag cgatggtgtagtagctggaatcgcggtgaggagtataactactggggcca ggggacccaggtcaccgtctcctca-3'

HIV1-2 (SEQ ID NO: 3):
5'-caggtgcagctggtggagtctgggggaggctcggtgcaggctggaga ctctctgagactctcctgtgcagcctctggaaacactgccagtaggttct ccatgggctggttccgccaggctccagggaaggagcgcgagggggtcgcg gctatttctgctggtggtaggcttacatactatgccgactccgtgaaggg ccgattcaccatctcccgagacaacgccaagaacacgctgtatctggaca tgaacaacctgaaacctgaggacactgccatgtactactgtgccgcaatt agtgaccggatgactggtattcaggctcttgcggctctacccagacttcg cccagaagactacggtaactggggccaggggaccctggtcaccgtctcct ca-3'

HIV1-7 (SEQ ID NO: 4):
5'-gaggtgcagctggtggagtctgggggagactcggtgcaggctgga gggtctcttcaactctcctgtaaagcctctggatacacctacaatagta gagtcgatatcagatctatgggctggttccgccagtatccaggaaagga gcgcgagggggtcgctactattaatattcgtaatagtgtcacatactat gccgactccgtgaagggccgattcaccatctcccaagacaacgccaaga acacggtgtatctgcaaatgaacgccctgaaacctgaggacactgccat gtactactgtgcgttgtcagacagattcgcggcgcaggtacctgccagg tacggaatacggccctctgactataactactggggtgaggggaccctgg tcaccgtctcctca-3'
```

-continued

```
HIV1-8 (SEQ ID NO: 5):
5'-caggtgcagctggtggagtctgggggagactcggtgcaggctggag ggtctcttcaactctcctgtaaagcctctggatacacctacaatagtag agtcgatatcagatctatgggctggttccgccagtatccaggaaaggag cgcgagggggtcgctactattaatattcgtaatagtgtcacatactatg ccgactccgtgaagggccgattcaccatctcccaagacaacgccaagaa cacggtgtatctgcaaatgaacgccctgaaacctgaggacactgccatg tactactgtgcgttgtcagacagattcgcggcgcaggtacctgccaggt acggaatacggccctctgactataactactggggccaggggacccaggt caccgtctcctca-3'

HIV1-6 (SEQ ID NO: 6):
5'-caggtgcagctggtggagtctgggggagactcggtgcaggctggag ggtctcttcaactctcctgtaaagcctctggatacacctacaatagtag agtcgatatcagatctatgggctggttccgccaatatccaggaaaggag cgcgagggggtcgctactattaatattcgtaatagtgtcacatactatg ccgactccgtgaagggccgattcaccatctcccaagacaacgccaagaa cacggtgtatctgcaaatgaacgccctgaaacctgaggacactgccat gtactactgtgcgttgtcagacagattcgcggcgcaggtacctgccagg tacggaatacggccctctgactataactactggggccaggggaccctgg tcaccgtctcctca-3'

HIV1_28 (SEQ ID NO: 7):
5'-aggtgcagctggtggagtctgggggagactcggtgcaggctggagg gtctcttcaactctcctgtaaagcctctggatacacctacaatagtaga gtcgatatcagatctatgggctggttccgccagtatccaggaaaggagc gcgagggggtcgctactattaatattcgtaatagtgtcacatactatgc cgactccgtgaagggccgattcaccatctcccaagacaacgccaagaac acggtgtatctgcaaatgaacgccctgaaacctgaggacactgccatgt actactgtgcgttgtcagacagattcgcggcgcaggtacctgccaggta cggaatacggccctctgactataactactggggccaggggaccctggtc accgtctcctca-3'

HIV1-21 (SEQ ID NO: 8):
5'-gaggtgcagctggtggagtctgggggagactcggtgcaggctggag ggtctcttcaactctcctgtaaagcctctggatacacctacaatagtag agtcgatatcagatctatgggctggttccgccagtatccaggaaaggag cgcgagggggtcgctactattaatattcgtaatagtgtcacatactatg ccgactccgtgaagggccgattcaccatctcccaagacaacgccaagaa cacggtgtatctgcaaatgaacgccctgaaacctgaggacactgccatg tactactgtgcgttgtcagacagattcgcggcgcaggtacctgccaggt acggaatacggccctctgactataactactggggtgaggggacccaggt caccgtctcctca-3'

HIV1-37 (SEQ ID NO: 9):
5'-gaggtgcagctggtggagtctgggggagactcggtgcaggctggag ggtctcttcaactctcctgtaaagcctctggatacacctacaatagtag
```

-continued agtcgatatcagatctatgggctggttccgccagtatccaggaaaggag cgcgagggggtcgctactattaatattcgtaatagtgtcacatactatg ccgactccgtgaagggccgattcaccatctcccaagacaacgccagaa cacggtgtatctgcaaatgaacgccctgaaacctgaggacactgccatg tactactgtgcgttgtcagacagattcgcggcgcaggtacctgccaggt acggaatacggccctctgactataactactggggtgaggggacccaggt caccgtctcctca-3'

HIV1-3 (SEQ ID NO: 10):
5'-gaggtgcagctggtggagtctgggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccagaacacgg tgtatctgcaaatgaacgccctgaaacctgaggacactgccatgtactac tgtgcgttgtcagacagattcgcggcgcaggtacctgccaggtacggaat acggccctctgactataactactggggtgaggggacccaggtcactgtct cctca-3'

HIV1-5 (SEQ ID NO: 11):
5'-gaggtgcagctggtggagtctgggggagactcggtgcaggctggagg gtctcttcaactctcctgtaaggcctctggatacacctacaatagtagag tcgatatcagatctatgggctggttccgccagtatccaggaaaggagcgc gagggggtcgctaccattaatattcgtaatagtgtcacatactatgccga ctccgtgaagggccgattcaccatctcccaagacaacgctaagaacacgg tgtatctgcaaatgaacgccctgaaacctgaggacactgccatgtactac tgtgcgttgtcagacagattcgcggcgcaggtacctgccaggtacggaat acggccctctgactataactactggggtgaggggacccaggtcaccgtct cctca-3'

HIV1-10 (SEQ ID NO: 12):
5'-gaggtgcagctggtggagtctgggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccagaacacgg tgtatctgcaaatgaacgccctgaaacctgaggacactgccatgtactac tgtgcgttgtcagacagattcgcagcgcaggtacctgccaggtacggaat acggccctctgactataactactggggtgaggggacccaggtcaccgtct cctca-3'

HIV1_29 (SEQ ID NO: 13):
5'-gaggtgcagctggtggagtctgggggagactcagtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccagaacacgg tgtatctgcaaatgaacgccctgaaacctgaggacactgccatgtactac tgtgcgttgtcagacagattcgcggcgcaggtacctgccaggtacggaat acggccctctgactataactactggggtgaggggacccaggtcaccgtct cctca-3'

HIV1_32 (SEQ ID NO: 14):
5'-gaggtgcagctggtggagtctgggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccagaacacgg tgtatctgcaaatgaacgccctgaaacctgaggacactgccatgtactac tgtgcgttgtcagacagattcgcggcgcaggtacctgccaggtacggaat acggccctctgactataactactggggtgaggggacccaggtcaccgtct cctca-3'

HIV1-9 (SEQ ID NO: 15):
5'-gaggtgcagctggtggagtctgggggaggctcggtgcaggctggagg gtctctgagactctcctgtgcagcctctgtttacagctacaacacaaact gcatgggttggttccgccaggctccagggaaggagcgcgagggggtcgca gttatttatgctgctggtggattaacatactatgccgactccgtgaaggg ccgattcaccatctcccaggagaatggcaagaacacggtgtacctgacga tgaaccgcctgaaacctgaggacactgccatgtactactgtgcggcaaag cgatggtgtagtagctggaatcgcggtgaggagtataactactggggcca ggggacccaggtcactgtctcctca-3'

HIV1-16 (SEQ ID NO: 16):
5'-caggtgcagctggtggagtctgggggaggctcggtgcaggctggagg gtctctgagactctcctgtgcagcctctggaaacacctacagtagtagct actgcatgggctggttccgccaggctccagggaaggaccgcgagggggtc gcgcgtattttcactcgaagtggtaccacatactatgccgactccgtgaa gggccgattcaccatttccgtgacaacgccagaacacggtgtatctgc aaatgaacagcctgaaacctgaagacgctgccatgtactactgtgcggca gcccagggggtgcctgcatttcgtttacttcgttcgcgaagaatttcgt gtaccggggccaggggaccctggtcactgtctcctca-3'

HIV1-13 (SEQ ID NO: 17):
5'-gaggtgcagctggtggagtctgggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccagaacacgg tgtatctgcaaatgaacgccctgaaacctgaggacactgccatgtactac tgtgcgttgtcagacagattcgcggcgcaggtacctgccaggtacggaat acggtcctctgactataactactggggtgaggggacccaggtcaccgtct cctca-3'

HIV1_35 (SEQ ID NO: 18):
5'-gaggtgcagctggtggagtctggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccaagaacacgg tgtatctgcaaatgaacgccctgaaacctgaggacactgccatgtactac tgtgcgttgtcagacagattcgcggcgcaggtacctgccaggtacggaat acggtcctctgactataactactggggtgaggggaccctggtcaccgtct cctca-3'

HIV1-11 (SEQ ID NO: 19):
5'-caggtgcagctggtggagtctggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccaagaacacgg tgtatctgcaaatgaacgccctgaaacctgaggacactgccatgtactac tgtgcgttgtcagacagattcgcggcgcaggtacctgccaggtacggaat acggccctctgactataactactggggtgaggggacccaggtcactgtct cctca-3'

HIV1_22 (SEQ ID NO: 20):
5'-caggtgcagctggtggagtctggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccaagaacacgg tgtatctgcaaatgaacgccctgaaacctgaggacactgccatgtactac tgtgcgttgtcagacagattcgcggcgcaggtacctgccaggtacggaat acggccctctgactataactactggggtgaggggacccaggtcaccgtct cctca-3'

HIV1-4 (SEQ ID NO: 21):
5'-catgtgcagctggtggagtctggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccaagaacacgg tgtatctgcaaatgaacgccctgaaacctgaggacactgccatgtactac tgtgcgttgtcagacagattcgcggcgcaggtacctgccaggtacggaat acggccctctgactataactactggggtgaggggaccctggtcaccgtct cctca-3'

HIV1_38 (SEQ ID NO: 22):
5'-gaggtgcagctggtggagtctggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccaa ctccgtgaagggccgattcaccatctcccaagacaacgccaagaacacgg tgtatctgcaaatgaacgccctgaaacctgaggacactgccatgtactac tgtgcgttgtcagacagattcgcggcgcaggtacctgccaggtacggaat acggccctctgactatgactactggggtgaggggaccctggtcaccgtc tcctca-3'

HIV1_23 (SEQ ID NO: 23):
5'-gaggtgcagctggtggagtctggggagactcggtgcaggctggagg gtctcttcaactctcctgtaaagcctctggatacacctacaatagtagag tcgatatcagatctatgggctggttccgccagtatccaggaaaggagcgc gagggggtcgctactattaatattcgtaatagtgtcacatactatgccga ctccgtgaagggccgattcaccatctcccaagacaacgccaagaacacgg tgtatctgcaaatggacgccctgaaacctgaggacactgccatgtactac tgtgcgttgtcagacagattcgcggcgcaggtacctgccaggtacggaat acggccctctgactataactactggggtgaggggacccaggtcaccgtct cctca-3'

HIV1_25 (SEQ ID NO: 24):
5'-gaggtgcagctggtggagtctggggagactcggtgcaggctggagg gtctcttcaactctcctgtaaggcctctggatacacctacaatagtagag tcgatatcagatctgtgggctggttccgccagtatccaggaaaggagcgc gagggggtcgctactattaatattcgtaatagtgtcacatactatgccga ctccgtgaagggccgattcaccatctcccaagacaacgccaagaacacgg tgtatctgcaaatgaacgccctgaaacctgaggacactgccatgtactac tgtgcgttgtcagacagattcgcggcgcaggtacctgccaggtacggaat acggccctctgactataactactggggtgaggggacccaggtcaccgtct cctca-3'

The amino acid sequences of the anti-HIV-1 RT sdAbs are shown below:

HIV1-1 (SEQ ID NO: 25):
DVQLVESGGGSVQAGGSLRLSCAASVYSYNTNC
MGWFRQAPGKEREGVAVIYAAGGLTYYADSVKGRFTISQENGKNTVYLTM
NRLKPEDTAMYYCAAKRWCSSWNRGEEYNYWGQGTQVTVSS

HIV1-2 (SEQ ID NO: 26):
QVQLVESGGGSVQAGDSLRLSCAASGNTASRFSM
GWFRQAPGKEREGVAAISAGGRLTYYADSVKGRFTISRDNAKNTLYLDMN
NLKPEDTAMYYCAAISDRMTGIQALAALPRLRPEDYGNWGQGTLVTVSS

HIV1-9 (SEQ ID NO: 27):
EVQLVESGGGSVQAGGSLRLSCAASVYSYNTNCM
GWFRQAPGKEREGVAVIYAAGGLTYYADSVKGRFTISQENGKNTVYLTMN
RLKPEDTAMYYCAAKRWCSSWNRGEEYNYWGQGTQVTVSS

HIV1-16 (SEQ ID NO: 28):
QVQLVESGGGSVQAGGSLRLSCAASGNTYSSSY
CMGWFRQAPGKDREGVARIFTRSGTTYYADSVKGRFTISRDNAKNTVYLQ
MNSLKPEDAAMYYCAAAQGGACISFTSFAKNFVYRGQGTLVTVSS

-continued

HIV1-27 (SEQ ID NO: 29):
EVQLGESGGGSVQAGGSLRLSCAASVYSYTTNCM
GWFRQAPGKEREGVAVIYSAGGLTYYADSVKGRFTISQDNGKNTVYLTMN
RLKPEDTAMYYCAAKRWCSSWNRGEEYNYWGQGTQVTVSS

HIV1-30 (SEQ ID NO: 30):
QVQLVESGGGSVQAGGSLRLSCAASVYSYNTN
CMGWFRQAPGKEREGAAVIYAAGGLTYYADSVKGRFTISQENGKNTVYLT
MNRLKPEDTAMYYCAAKRWCSSWNRGEEYNYWGQGTQVTVSS

HIV1-21 (SEQ ID NO: 31):
EVQLVESGGDSVQAGGSLQLSCKASGYTYNSR
VDIRSMGWFRQYPGKEREGVATINIRNSVTYYADSVKGRFTISQDNAKNT
VYLQMNALKPEDTAMYYCALSDRFAAQVPARYGIRPSDYNYWGEGTQVTV
SS

HIV1-4 (SEQ ID NO: 32):
HVQLVESGGDSVQAGGSLQLSCKASGYTYNSR
VDIRSMGWFRQYPGKEREGVATINIRNSVTYYADSVKGRFTISQDNAKN
TVYLQMNALKPEDTAMYYCALSDRFAAQVPARYGIRPSDYNYWGEGTLV
TVSS

HIV1-6 (SEQ ID NO: 33):
QVQLVESGGDSVQAGGSLQLSCKASGYTYNSRVD
IRSMGWFRQYPGKEREGVATINIRNSVTYYADSVKGRFTISQDNAKNTVY
LQMNALKPEDTAMYYCALSDRFAAQVPARYGIRPSDYNYWGQGTLVTVSS

HIV1-7 (SEQ ID NO: 34):
EVQLVESGGDSVQAGGSLQLSCKASGYTYNSRVD
IRSMGWFRQYPGKEREGVATINIRNSVTYYADSVKGRFTISQDNAKNTVY
LQMNALKPEDTAMYYCALSDRFAAQVPARYGIRPSDYNYWGEGTLVTVSS

HIV1-8 (SEQ ID NO: 35):
QVQLVESGGDSVQAGGSLQLSCKASGYTYNSRVD
IRSMGWFRQYPGKEREGVATINIRNSVTYYADSVKGRFTISQDNAKNTVY
LQMNALKPEDTAMYYCALSDRFAAQVPARYGIRPSDYNYWGQGTQVTVSS

HIV1-11 (SEQ ID NO: 36):
QVQLVESGGDSVQAGGSLQLSCKASGYTYNSRVD
IRSMGWFRQYPGKEREGVATINIRNSVTYYADSVKGRFTISQDNAKNTVY
LQMNALKPEDTAMYYCALSDRFAAQVPARYGIRPSDYNYWGEGTQVTVSS

HIV1-13 (SEQ ID NO: 37):
EVQLVESGGDSVQAGGSLQLSCKASGYTYNSRVD
IRSMGWFRQYPGKEREGVATINIRNSVTYYADSVKGRFTISQDNAKNTVY
LQMNALKPEDTAMYYCALSDRFAAQVPARYGIRSSDYNYWGEGTLVTVSS

HIV1-23 (SEQ ID NO: 38):
EVQLVESGGDSVQAGGSLQLSCKASGYTYNSRVD
IRSMGWFRQYPGKEREGVATINIRNSVTYYADSVKGRFTISQDNAKNTVY
LQMDALKPEDTAMYYCALSDRFAAQVPARYGIRPSDYNYWGEGTQVTVSS

HIV1-24 (SEQ ID NO: 39):
HVQLVESGGDSVQAGGSLQLSCKASGYTYNSRVD
IRSMGWFRQYPGKEREGVATINIRNSVTYYADSVKGRFTISQDNAKNTVY
LQMNALKPGDTAMYYCALSDRFAAQVPARYGIRPSDYNYWGQGTLVTVSS

HIV1-25 (SEQ ID NO: 40):
EVQLVESGGDSVQAGGSLQLSCKASGYTYNSRVD
IRSVGWFRQYPGKEREGVATINIRNSVTYYADSVKGRFTISQDNAKNTVY
LQMNALKPEDTAMYYCALSDRFAAQVPARYGIRPSDYNYWGEGTQVTVSS

HIV1-31 (SEQ ID NO: 41):
DVQLVESGGDSVQAGGSLQLSCKASGYTYNSRVD
IRSMGWFRQYPGKEREGVATINIRNSVTYYADSVKGRFTISQDNAKNTVY
LQMNALKPEDTAMYYCALSDRFAAQVPARYGIRPSDYNYWGEGTQVTVSS

HIV1-38 (SEQ ID NO: 42):
EVQLVESGGDSVQAGGSLQLSCKASGYTYNSRVD
IRSMGWFRQYPGKEREGVATINIRNSVTYYANSVKGRFTISQDNAKNTVY
LQMNALKPEDTAMYYCALSDRFAAQVPARYGIRPSDYDYWGEGTLVTVSS

HIV1-39 (SEQ ID NO: 43):
EVQLVESGGDSVQAGGSLQLSCKASGYTYNSRVD
IRSMGWFRQYPGKEREGVATINIRNSVTYYADSVKGRFTISQDNAKNTVY
LQMNALKPEDTAMYYCALSDRFAAQVPTRYGIRPSDYNYWGQGTQVTVSS

One or more mouse monoclonal antibodies can be generated against one or more domains of the anti-HIV-1 RT sdAbs of the invention. The mouse monoclonal antibody can be generated by methods that are known by one of skill in the art, for example, the mouse monoclonal antibody can be produced by a mouse hybridoma. The mouse monoclonal antibody can be used in diagnostic assays, for example, the antibody can be used in an immunoassay such as an ELISA or mass spectrometry assay in order to measure the amount of anti-HIV-1 RT sdAb present in a sample from a patient.

SdAbs were also generated against a recombinant Arachidonate 12-lipoxygenase (ALOX12). ALOX12 is also known as platelet-type 12-lipoxygenase, arachidonate oxygen 12-oxidoreductase, Delta12-lipoxygenase, 12Delta-lipoxygenase, C-12 lipoxygenase, leukotriene A4 synthase, and LTA4 synthase. ALOX12 is a lipoxygenase-type enzyme that participates in arachidonic acid metabolism. ALOX12 has been implicated in the development and complications of dietary-induced and/or genetically-induced diabetes, adipose cell/tissue dysfunction, and obesity. ALOX12 has also been thought to regulate blood vessel contraction, dilation, pressure, remodeling, and angiogenesis. Inhibition of ALOX12 prevents the development of blood vessel formation and thus ALOX12 is a target for reducing neo-vascularization that promotes atherosclerosis, Steatohepatitis, and other arthritic and cancer diseases. Elevated amounts of ALOX12 may contribute to the development of Alzheimer's disease.

The present invention provides sdAbs, proteins, and polypeptides that are directed against the ALOX12 protein.

It is contemplated that the anti-ALOX12 sdAbs and polypeptides of the invention can be used for the prevention and/or treatment of diseases and disorders associated with and/or mediated by ALOX12, such as diabetes, adipose cell dysfunction, obesity, atherosclerosis, Steatohepatitis, arthritis and cancer.

Recombinant human ALOX12 protein was used to generate sdAbs that are directed against or can bind to an epitope of ALOX12. To generate the anti-ALOX12 sdAbs, recombinant human ALOX12 was expressed in *Escherichia coli* and used as the target antigen.

The recombinant ALOX12 protein sequence (SEQ ID NO:44) used for immunization of camels was:

MGRYRIRVATGAWLFSGSYNRVQLWLVGTRGEAELELQLRPARGEEEEFD

HDVAEDLGLLQFVRLRKHHWLVDDAWFCDRITVQGPGACAEVAFPCYRWV

QGEDILSLPEGTARLPGDNALDMFQKHREKELKDRQQIYCWATWKEGLPL

TIAADRKDDLPPNMRFHEEKRLDFEWTLKAGALEMALKRVYTLLSSWNCL

EDFDQIFWGQKSALAEKVRQCWQDDELFSYQFLNGANPMLLRRSTSLPSR

LVLPSGMEELQAQLEKELQNGSLFEADFILLDGIPANVIRGEKQYLAAPL

VMLKMEPNGKLQPMVIQIQPPNPSSPTPTLFLPSDPPLAWLLAKSWVRNS

DFQLHEIQYHLLNTHLVAEVIAVATMRCLPGLHPIFKFLIPHIRYTMEIN

TRARTQLISDGGIFDKAVSTGGGGHVQLLRRAAAQLTYCSLCPPDDLADR

GLLGLPGALYAHDALRLWEIIARYVEGIVHLFYQRDDIVKGDPELQAWCR

EITEVGLCQAQDRGFPVSFQSQSQLCHFLTMCVFTCTAQHAAINQGQLDW

YAWVPNAPCTMRMPPPTTKEDVTMATVMGSLPDVRQACLQMAISWHLSRR

QPDMVPLGHHKEKYFSGPKPKAVLNQFRTDLEKLEKEITARNEQLDWPYE

YLKPSCIENSVTI

As a result of the immunization, several sdAbs were obtained and screened. The DNA sequences of the sdAbs are listed below:

ALOX_21 (SEQ ID NO: 45):
5'-gaggtgcagctggtggagtctggggaggttcggtgcagg ctggagggtctctgaggatctcctgtacagcctctggattcactttga tgacactgacatgggctggtaccgccagactctaggaaatgggtgcgag ttggtttctcagattagtaatgatggtagtacattctatagagattccg tgaagggccgattcaccatctcctgggaccgcgtcaacaacacggtgta tctgcaaatgagcgccctgagacctgaggacacggccatgtattactgc aatatcaacgggtgtaggagaccctcgtacaatcttcacttgaacgcat ggggccaggggacacaggtcaccgtctcctca-3'

ALOX_41 (SEQ ID NO: 46):
5'-caggtgcagctggtggagtctggggaggctcggtgcagg ctggagggtctctgacactgtcctgtgtagcctctggatacggctacag tgccacgtgcatgggctggttccgccaggctccagggaaggagcgcgag ggggtcgcgtctatttcacttatggtgttagaaccttctatgccgact ccgcgaaaggccgattcaccgtctcccgagacaacgccaagaacacgct gtatctgcaaatgaacagcctgaaacctgaggacacgtccgtgtactac tgtgcggccggttcgggcgttggtgtttgttcactttcgtatccataca cctactggggccaggggacccaggtcaccgtctcctca-3'

ALOX_43 (SEQ ID NO: 47):
5'-caggtgcagctggtggagtctggggaggctcggtgcgg gctggagagtctctgagactctcctgtgtagcctctagatccatctatg tttggtactgcatgggctggttccgccaggctgcagggaaggagcgcga ggggtcggaagtatgttcgttggtggcggtaggacatattatgacgac tccgtcaagggccgattcaccatctcccaagacaaggccaagaacacgc tgtatctgcaaatggacaacctggcacctgaagacactgccatgtatta ctgtgcggctgggcgctgcggtggcaactggctgagaagcaatgctttc gacaaatggggccaggggacactggtcaccgtctcctca-3'

ALOX_46 (SEQ ID NO: 48):
5'-gatgtgcagctggtggagtctggggaggctcggtgcagg ctggagggtctctgagactctcctgtcagccactggaaacacctacat tagccgctgcatgggctggttccgccagcctccagggaaggagcgcgag gtggtcgcacgtatttataccgactctggtaatacatactatcccgacg ccgtggagggccgattcaccatctcccaagacaacgccaagaacacgat atatctgcaaatgaacagcctgaaacctgacgacaccgccgtgtactac tgtgtgctctcagaggccgtctgtacaaaagaacctggggactttcgtt actggggccaggggacccaggtcactgtctcctca-3'

The protein sequences of the anti-ALOX sdAbs generated are as follows:

ALOX_21 (SEQ ID NO: 49):
EVQLVESGGGSVQAGGSLRISCTAS
GFTFDDTDMGWYRQTLGNGCELVSQISNDGSTFYRDSVKGRFTISWDRVN
NTVYLQMSALRPEDTAMYYCNINGCRRPSYNLHLNAWGQGTQVTVSS

ALOX_41 (SEQ ID NO: 50):
QVQLVESGGGSVQAGGSLTLSCVAS
GYGYSATCMGWFRQAPGKEREGVASISPYGVRTFYADSAKGRFTVSRDNA
KNTLYLQMNSLKPEDTSVYYCAAGSGVGVCSLSYPYTYWGQGTQVTVSS

ALOX_43 (SEQ ID NO: 51):
QVQLVESGGGSVRAGESLRLSCVAS
RSIYVWYCMGWFRQAAGKEREGVGSMFVGGGRTYYDDSVKGRFTISQDKA
KNTLYLQMDNLAPEDTAMYYCAAGRCGGNWLRSNAFDKWGQGTLVTVSS

ALOX_46 (SEQ ID NO: 52):
DVQLVESGGGSVQAGGSLRLSCAAT
GNTYISRCMGWFRQPPGKEREVVARIYTDSGNTYYPDAVEGRFTISQDNA
KNTIYLQMNSLKPDDTAVYYCVLSEAVCTKEPGDFRYWGQGTQVTVSS

One or more mouse monoclonal antibodies can be generated against one or more domains of the anti-ALOX12 sdAbs of the invention. The mouse monoclonal antibody can be generated by methods that are known by one of skill in the art, for example, the mouse monoclonal antibody can be produced by a mouse hybridoma. The mouse monoclonal antibody can be used in diagnostic assays, for example, the antibody can be used in an immunoassay such as an ELISA or mass spectrometry assay in order to measure the amount of anti-ALOX12 sdAb present in a sample from a patient.

Ebola, also known as Ebola virus disease (EVD) and Ebola hemorrhagic fever (EHF), is a viral hemorrhagic fever of humans and other primates caused by Ebolavirus. The disease has a high risk of death, killing between 25 and 90 percent of those infected, typically six to sixteen days after symptoms appear.

Ebola interferes with proper functioning of the infected individual's innate immune system. Ebola proteins weaken the immune system's response to viral infections by interfering with the cells ability to produce and respond to interferon proteins such as interferon-alpha, interferon-beta, and interferon gamma. Ebola's structural proteins, VP24 and VP35, play a key role in this interference. The V24 protein blocks the production of the host cell's antiviral proteins. By inhibiting the host's immune responses, Ebola quickly spreads throughout the body.

As described herein, anti-VP24 sdAbs were developed to target Ebola's VP24 protein. The anti-VP24 sdAb may successfully treat individuals infected with Ebola either alone or in combination with other retroviral agents. Using methods that are well-known in the art, recombinant VP24 protein (SEQ ID NO:53) was used to generate sdAbs that are directed against or can bind to an epitope of VP24.

The protein sequence recombinant VP24 protein (SEQ ID NO:53) used for immunization of a camel was:

AKATGRYNLISPKKDLEKGVVLSDLCNFLVSQTIQGWKVYWAGIEFDVTH

KGMALLHRLKTNDFAPAWSMTRNLFPHLFQNPNSTIESPLWALRVILAAG

IQDQLIDQSLIEPLAGALGLISDWLLTTNTNHFNMRTQRVKEQLSLKMLS

LIRSNILKFINKLDALHVVNYNGLLSSIEIILEFNSSLAI

As a result of the immunization, one anti-VP24 sdAb, VP24_5 was obtained and screened for binding to VP24. The DNA sequence of VP24_5 (SEQ ID. NO:54) is:

5'-ATGGGTGAT GTGCAGCTGGTGGAGTCT GGGGGAGAC

TCGGTGCGG GCTGGAGGGG TCTCTTCAAATGGGTGAT GTGCAGCTG

GTGGAGTCT GGGGGAGAC TCGGTGCGGGCTGGAGGGTCTCTTCAA

-continued

```
CTCTCCTGT AAAGCCTCT GGATACACC

TACAATAGTAGAGTCGATATCAGATCT ATGGGCTGG TTCCGCCAG

TATCCAGGA AAGGAGCGCGAGGGGGTCGCTACTATT AATATTCGT

AATAGTGTC ACATACTAT GCCGACTCCGTGAAGGGCCGATTCACC

ATCTCCCAA GACAACGCC AAGAACACG

GTGTATCTGCAAATGAACGCCCTGAAA CCTGAGGAC ACTGCCATG

TACTACTGT GCGTTGTCAGACAGATTCGCGGCGCAG GTACCTGCC

AGGTACGGA ATACGGCCC TCTGACTAT AACTACTGG GGTGAGGGG

ACCCTGGTC ACCGTCTCC TCAAGCTCT GGTCTCGAG-3'
```

The amino acid sequence of the VP24_5 sdAb (SEQ ID NO:55) is shown below, with the CDRs underlined:

MGDVQLVESGGDSVRAGGSLQLSCKASGYTYNSRVD<u>IRSMG</u>WFRQYPGK
EREGVA<u>TINIRNSVTYYADSVKGR</u>FTISQDNAKNTVYLQMNALKPEDTA
MYYCAL<u>SDRFAAQVPARYGIRPSDYNY</u>WGEGTLVTVSSSSGLE

One or more mouse monoclonal antibodies can be generated against one or more domains of the anti-VP24 sdAb of the invention. The mouse monoclonal antibody can be generated by methods that are known by one of skill in the art, for example, the mouse monoclonal antibody can be produced by a mouse hybridoma. The mouse monoclonal antibody can be used in diagnostic assays, for example, the antibody can be used in an immunoassay such as an ELISA or mass spectrometry assay in order to measure the amount of anti-VP24 sdAb present in a sample from a patient.

EXAMPLES

Example 1: Generation of sdAbs

SdAbs were produced from a camel that was immunized with several proteins including ALOX12 (SEQ ID NO:44), VP24 (SEQ ID NO:53), and HIV-1 reverse transcriptase (SEQ ID NO:1).

Using standard techniques, a phage display library was constructed using the pCDisplay-3M vector (Creative Biogene, Shirley, N.Y.) and M13K07 helper phage (New England Biolabs, Ipswich, Mass.). Single clones of sdAbs were confirmed by ELISA, and the DNA and protein sequences determined using standard methods.

Example 2: HIV1-9 (SEQ ID NO:27) sdAb Binds HIV-1 Reverse Transcriptase and Ebola VP-24

Protein binding experiments were performed on a Biacore 3000 (General Electric Company, Fairfield, Conn.) at 25° C. The assay buffer contained 10 mM HEPES buffer (pH 7.4), 150 mM NaCl, 3 mM EDTA, 0.05% P20. The regeneration buffer contained 10 mM glycine HCl pH 1.75, and the immobilization buffer contained 10 mM sodium acetate, pH 5.0. The flow rate used for capturing the ligand was 5 ul/min. The flow rate used for kinetics analysis was 30 ul/min.

The ligands used for the protein binding experiment were HIV1-9 (SEQ ID NO:27) and STAT3-VHH 14 (SEQ ID NO:56). The ligands were directly immobilized by amine coupling (EDC/NHS) at a response unit (RU) of 1200 and 550 on flow cell 2 and 4, respectively, of a CM5 sensor chip. Flow cell 1 was kept blank and used for background subtraction. The un-occupied sites on the CM5 chip were blocked with 1M ethanol amine. For binding analysis, the analyte, rHIV-1 (SEQ ID NO:1) was flowed over the sensor chip. Binding of analyte to the ligand was monitored in real time. The affinity constant ($K_D$=kd/ka) was calculated from the observed on rate (ka) of off rate (kd), as shown in Table 1.

The negative control for the protein binding experiments was an anti-STAT3 sdAb, VHH14 (SEQ ID NO:56): QVQLVESGGGSVQAGGSLRLSCVASTYTGCMGW-FRQ APGKEREGVAALSSRGFAGHYTDSVKGRF-SISRDYVKNAVYLQMNTVKPEDAAMYYC AAREG-WECGETWLDRTAGGHTYWGQGTLVTVSS Chi square ($\chi^2$) analysis was carried out between the actual sensorgram and the sensorgram generated from the BIAnalysis software to determine the accuracy of the analysis. A $\chi^2$ value within 1-2 is considered accurate and below 1 is highly accurate.

TABLE 1

| Ligand | Analyte | ka (1/Ms) | kd (1/s) | Rmax | KD (M) | Conc. (nM) | Chi square |
|---|---|---|---|---|---|---|---|
| HIV1-9 VHH | rHIV-1 | $8.91 \times 10^4$ | $3.79 \times 10^{-4}$ | 71.3 | $4.25 \times 10^{-9}$ | 100 | 0.0321 |
| STAT3 VHH14 | rHIV-1 | N/A | N/A | N/A | N/A | 100 | N/A |

Full kinetic analysis was performed at analyte concentrations as indicated in Table 2 with 2 fold serial dilution of the highest analyte concentration. The HIV1-9 anti-RT sdAb bound both HIV-1 and Ebola VP24 analytes.

TABLE 2

| Ligand | Analyte | ka (1/Ms) | kd (1/s) | Rmax | KD (M) | Conc. (nM) | Chi square |
|---|---|---|---|---|---|---|---|
| HIV1-9 VHH (1200 RU) | rHIV-1 | $1.90 \times 10^5$ | $7.31 \times 10^{-4}$ | 126 | $3.85 \times 10^{-9}$ | 0-200 | 0.226 |
| STAT3 VHH14 (550 RU) | rHIV-1 | NA | NA | NA | NA | 0-200 | NA |
| HIV1-9 VHH (1200 RU) | VP-24 | $4.38 \times 10^2$ | $1.66 \times 10^{-4}$ | 1190 | $3.79 \times 10^{-7}$ | 0-200 | 0.199 |

Figure 2:
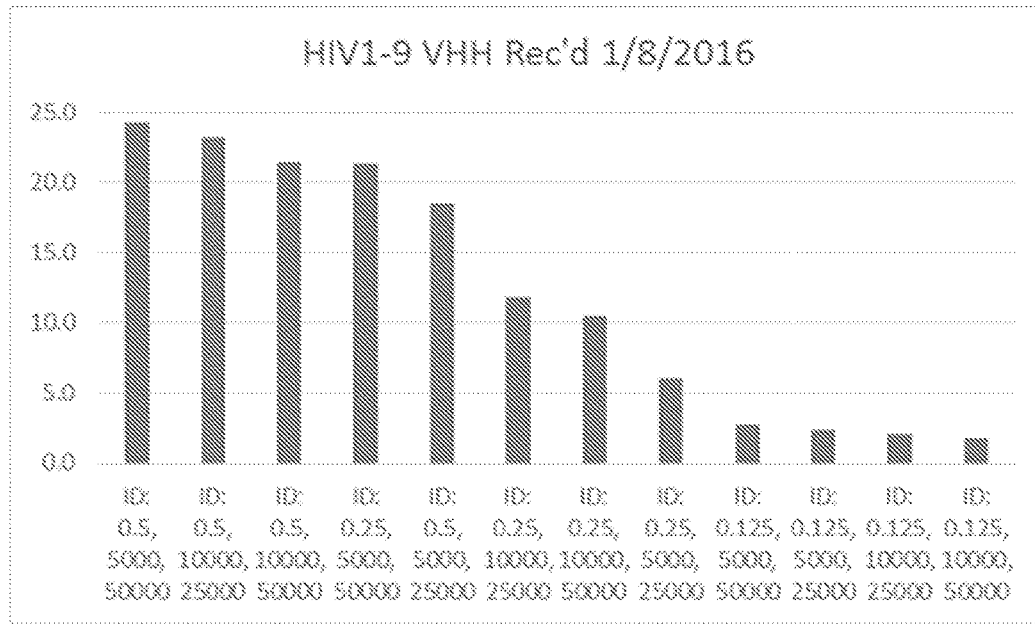

Example 3: HIV1-9 (SEQ ID NO:27) sdAb Binds HIV-1 Reverse Transcriptase in ELISA Two different samples of the HIV1-9 anti-HIV-1 RT sdAb (SEQ ID NO:27) was assessed at 1 µg/mL against a checkerboard of coating antigen, 2° antibody and HRP concentrations in an ELISA. The coating antigen was recombinant HIV-1 RT (Creative BioMart) (SEQ ID NO:1) at 0.5, 0.025 and 0.125 µg/mL per well. The secondary antibody was a rabbit anti-llama biotinylated diluted at 1:5,000, and 1:10,000, HRP at 1:25,000 and 1:50,000. Signal-to-noise ratios>20 were seen with several of the concentrations. The results of the ELISA are shown in FIGS. 1 and 2.

Three combinations were chosen to assess a dilution series of the HIV1-9 anti-HIV-1 RT sdAb (SEQ ID NO:27) (1 µg/mL to 0.0001 µg/mL).

| Coating Antigen | 2° antibody | HRP |
| --- | --- | --- |
| 0.5 µg/mL | 1:10,000 | 1:25,000 |
| 0.5 µg/mL | 1:5,000 | 1:50,000 |
| 0.5 µg/mL | 1:10,000 | 1:50,000 |

Figure 3:
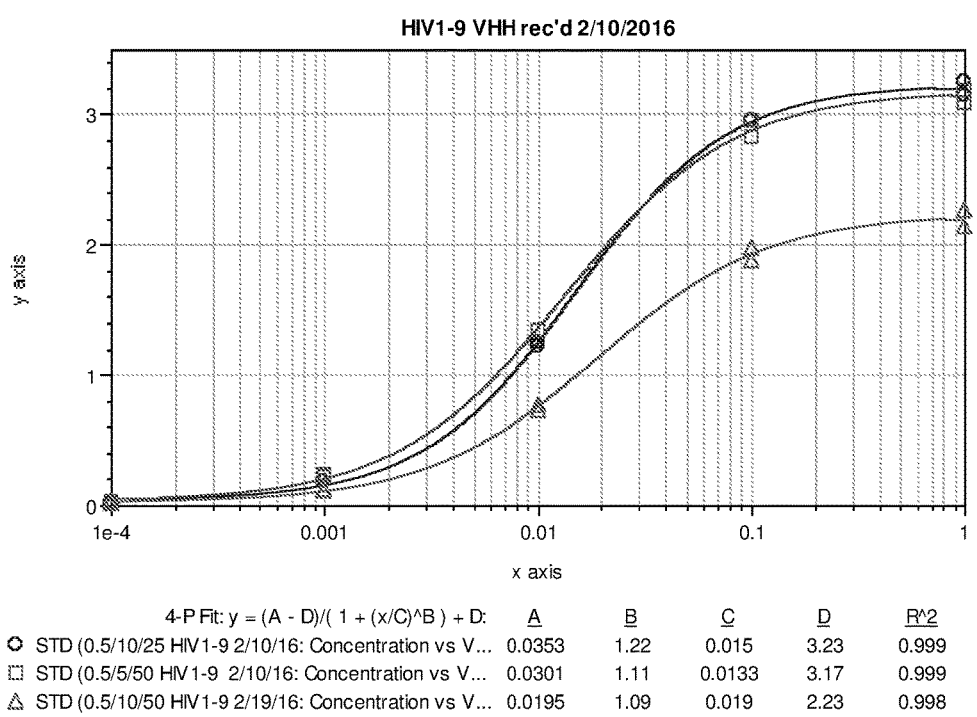
Figure 4:
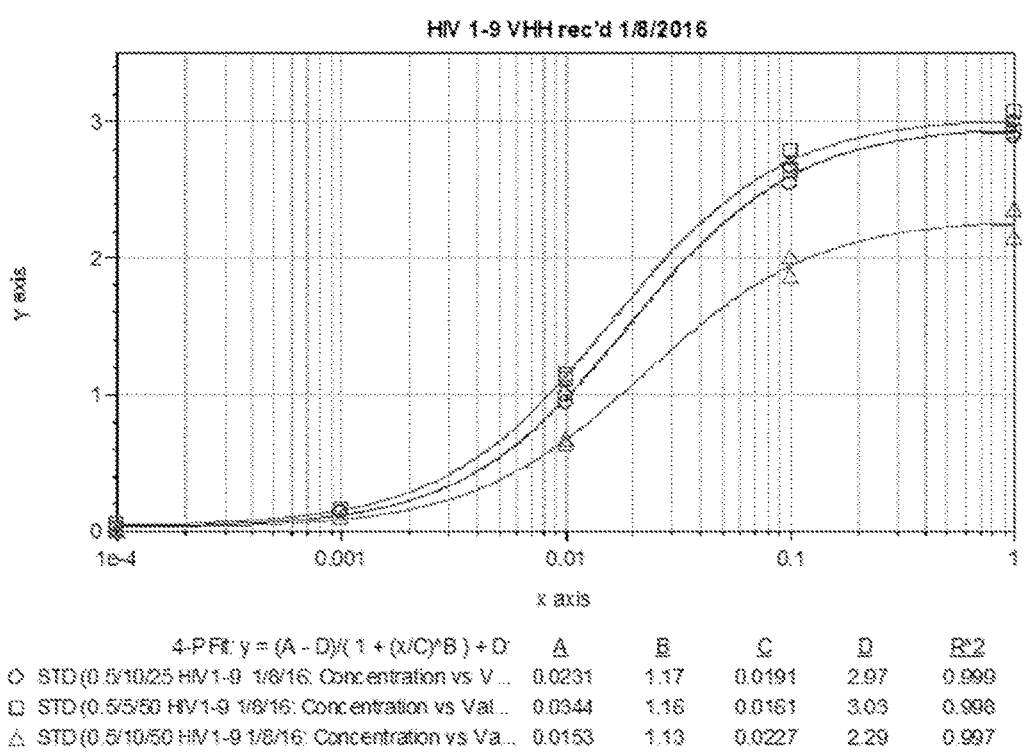

The results are shown in FIGS. 3 and 4. The two HIV1-9 anti-HIV-1 RT sdAb (SEQ ID NO:27) preparations used have very similar results. Results with 0.5 µg/mL coating, 1:5,000 dilution of 2° antibody and 1:50,000 dilution of HRP showed binding of HIV1-9 anti-HIV-1 RT sdAb (SEQ ID NO:27) to HIV1 RT (SEQ ID NO:1) with the highest signal-to-noise ratio and a slightly lower blank value.

Example 4: VP24-5 (SEQ ID NO:55) sdAb Binds VP24

Protein binding experiments were performed as described in Example 2. The ligands used for protein binding were VP24-5 (SEQ ID NO:55) and STAT3-VHH 14 (SEQ ID NO:56). The ligands were directly immobilized by amine coupling (EDC/NHS) at a response unit (RU) of 427 and 550 on flow cell 2 and 4, respectively, of a CM5 sensor chip. Flow cell 1 was kept blank and used for background subtraction. The un-occupied sites on the CM5 chip were blocked with 1M ethanol amine. For binding analysis, the analytes, VP24 (SEQ ID NO:53) was flowed over the sensor chip and monitored in real time. The affinity constant ($K_D$=kd/ka) was calculated from the observed on rate (ka) of off rate (kd), as shown in Table 3.

TABLE 3

| Ligand | Analyte | ka (1/Ms) | kd (1/s) | Rmax | KD (M) | Conc. (nM) | Chi2 |
| --- | --- | --- | --- | --- | --- | --- | --- |
| VP24-5-VHH | VP-24 | $1.39 \times 10^5$ | $8.77 \times 10^{-4}$ | 6.84 | $6.31 \times 10^{-9}$ | 100 | 0.0481 |
| STAT3 VHH14 | VP-24 | NA | NA | NA | NA | 100 | NA |

Full kinetic analysis was performed at different analyte concentrations with 2 fold serial dilution of the highest analyte concentration, as shown in Table 4.

TABLE 4

| Ligand | Analyte | ka (1/Ms) | kd (1/s) | Rmax | KD (M) | Conc. (nM) | Chi2 |
| --- | --- | --- | --- | --- | --- | --- | --- |
| VP24-5-VHH | VP-24 | $1.61 \times 10^3$ | $4.73 \times 10^{-5}$ | 222 | $2.94 \times 10^{-8}$ | 0-200 | 0.187 |
| STAT3 VHH14 (550 RU) | VP-24 | NA | NA | NA | NA | 0-200 | NA |

Example 5: VP24-5 (SEQ ID NO:55) sdAb Binds Ebola VP24 Target in ELISA

Two different samples of the VP24-5 anti-Ebola VP24 sdAb (SEQ ID NO:55) was assessed at 1 µg/mL against a checkerboard of coating antigen, 2° antibody and HRP concentrations in an ELISA. The coating antigen was recombinant Ebola VP24 (Creative BioMart) (SEQ ID NO:53) at 0.5, 0.025 and 0.125 µg/mL per well. The secondary antibody was a rabbit anti-llama biotinylated diluted at 1:5,000, and 1:10,000. HRP was used at a dilution of 1:10,000 and 1:25,000. The results of the ELISA are shown in FIGS. 5 and 6. The signal-to-noise ratios were low and the analysis was repeated with higher concentrations.

Figure 7:
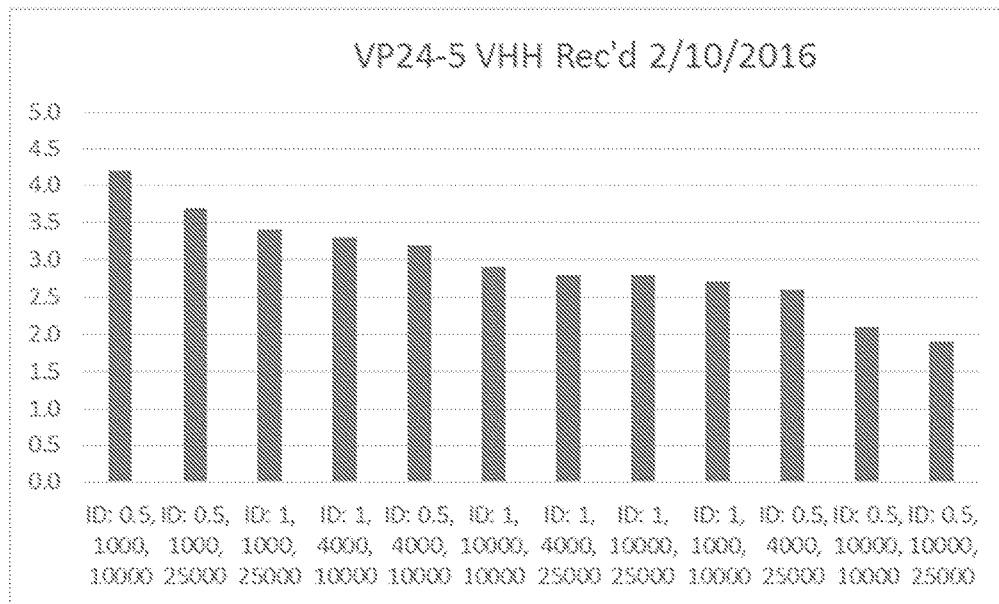
Figure 8:
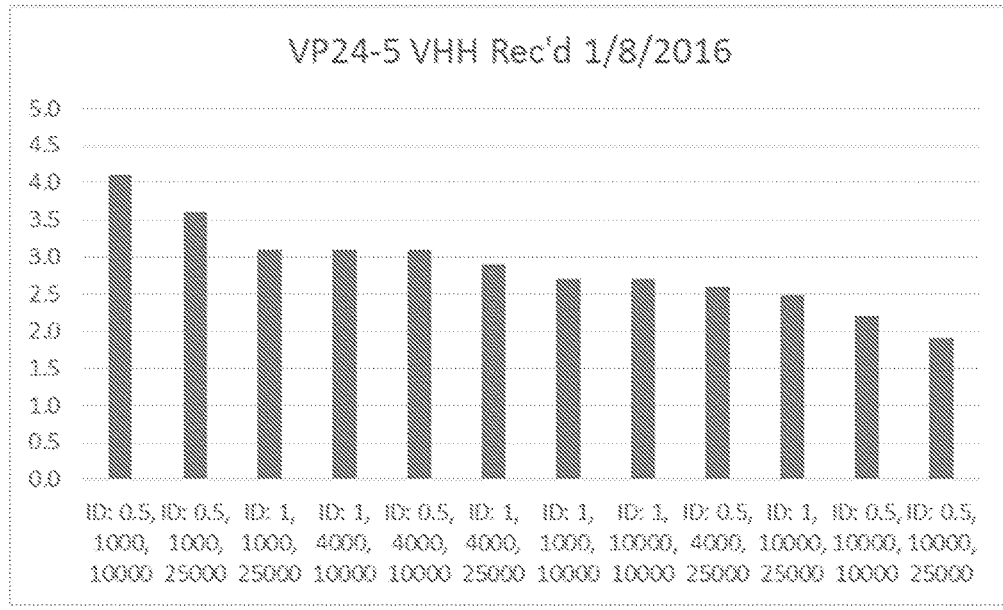

The ELISA was repeated with 1 and 0.5 µg/mL VP24-5 anti-Ebola VP24 sdAb (SEQ ID NO:55). Recombinant VP24 (SEQ ID NO:53) was used at either 0.5 or 1 µg/mL per well. The secondary antibody was a rabbit anti-llama biotinylated diluted at 1:1,000, 1:4,000, 1:10,000, and 1:10,000. HRP was used at a dilution of 1:25,000 and 1:50,000. The results of the ELISA are shown in FIGS. 7 and 8.

Three combinations were chosen to assess a dilution series of the VP24-5 anti-Ebola VP24 sdAb (SEQ ID NO:55) (1 µg/mL to 0.0001 µg/mL).

| Coating Antigen | 2° antibody | HRP |
| --- | --- | --- |
| 0.5 µg/mL | 1:1,000 | 1:1,000 |
| 0.5 µg/mL | 1:10,000 | 1:25,000 |
| 1 µg/mL | 1:4,000 | 1:25,000 |

Figure 9:
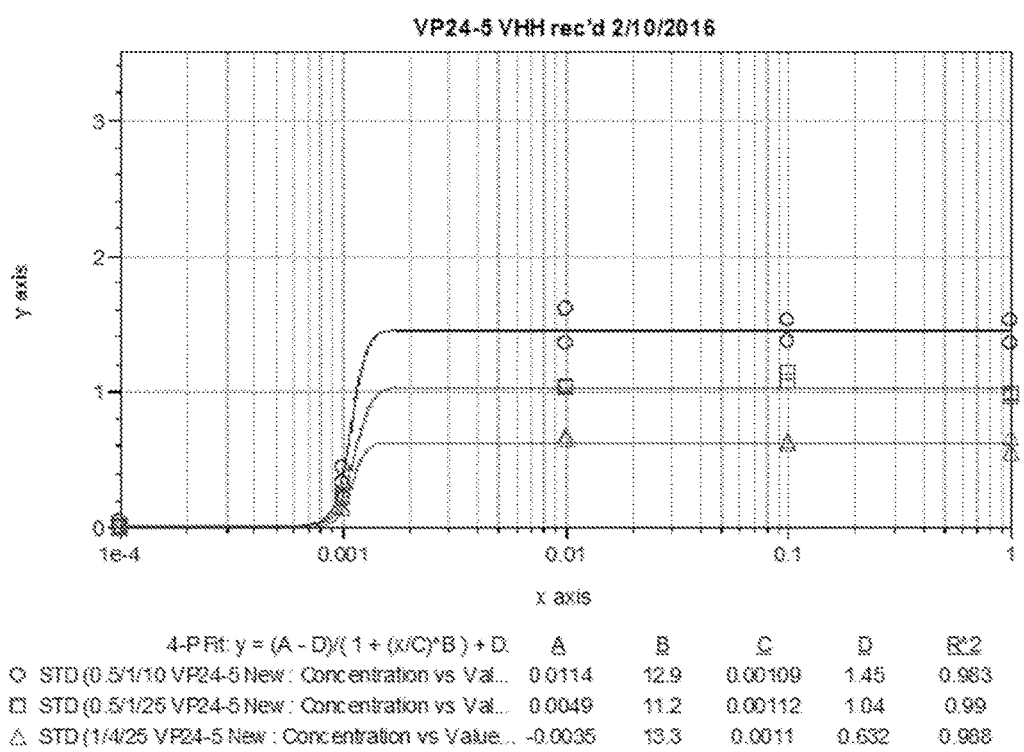
Figure 10:
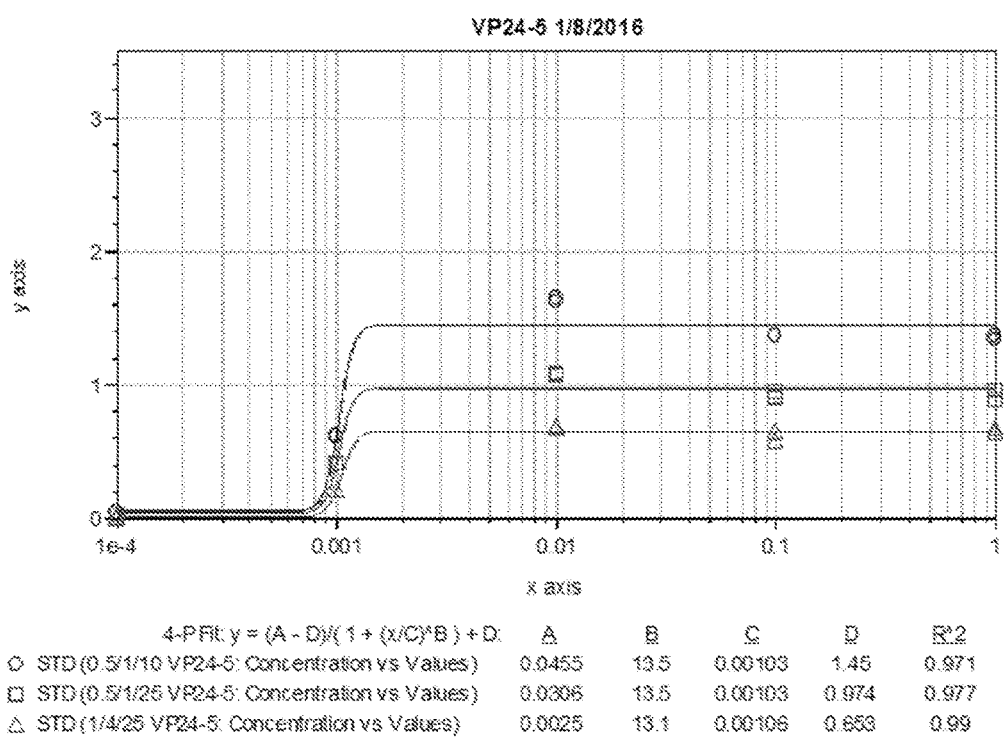

The results are shown in FIGS. 9 and 10. The two VP24-5 anti-Ebola VP24 sdAb (SEQ ID NO:55) preparations used have very similar results, and show binding of VP24-5 anti-Ebola VP24 sdAb (SEQ ID NO:55) to recombinant VP24 (SEQ ID NO:53).

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. An anti-HIV-1 reverse transcriptase sdAb, wherein the anti-HIV-1 reverse transcriptase sdAb comprises the amino acid sequence as set forth in SEQ ID NO: 27.

2. An isolated polypeptide, the isolated polypeptide comprising the amino acid sequence as set forth in SEQ ID NO: 27.

* * * * *